United States Patent
Sahin et al.

(10) Patent No.: US 12,385,049 B2
(45) Date of Patent: Aug. 12, 2025

(54) MODIFICATION OF RNA, PRODUCING AN INCREASED TRANSCRIPT STABILITY AND TRANSLATION EFFICIENCY

(71) Applicant: BioNTech SE, Mainz (DE)

(72) Inventors: Ugur Sahin, Mainz (DE); Silke Holtkamp, Mainz (DE); Ozlem Tureci, Mainz (DE); Sebastian Kreiter, Mainz (DE)

(73) Assignee: BioNTech SE, Mainz (DE)

( * ) Notice: Subject to any disclaimer, the term of this patent is extended or adjusted under 35 U.S.C. 154(b) by 0 days.

(21) Appl. No.: 18/049,593

(22) Filed: Oct. 25, 2022

(65) Prior Publication Data

US 2023/0193296 A1  Jun. 22, 2023

Related U.S. Application Data

(60) Division of application No. 16/143,520, filed on Sep. 27, 2018, now abandoned, which is a continuation of application No. 15/217,555, filed on Jul. 22, 2016, now Pat. No. 10,106,800, which is a division of application No. 11/992,638, filed as application No. PCT/EP2006/009448 on Sep. 28, 2006, now Pat. No. 9,476,055.

(30) Foreign Application Priority Data

Sep. 28, 2005  (DE) .................. 10 2005 046 490.4

(51) Int. Cl.
C12N 15/00 (2006.01)
C12N 15/67 (2006.01)
C12N 15/68 (2006.01)
C12N 15/85 (2006.01)

(52) U.S. Cl.
CPC ............ *C12N 15/68* (2013.01); *C12N 15/67* (2013.01); *C12N 15/85* (2013.01)

(58) Field of Classification Search
CPC ......... C12N 15/68; C12N 15/67; C12N 15/85
See application file for complete search history.

(56) References Cited

U.S. PATENT DOCUMENTS

| | | |
|---|---|---|
| 4,897,355 A | 1/1990 | Eppstein et al. |
| 5,264,618 A | 11/1993 | Felgner et al. |
| 5,703,055 A | 12/1997 | Felgner et al. |
| 6,251,399 B1 | 6/2001 | Diamond et al. |
| 6,472,176 B2 | 10/2002 | Kovesdi et al. |
| 6,500,641 B1 | 12/2002 | Chen et al. |
| 6,586,410 B1 | 7/2003 | Wheeler et al. |
| 7,303,881 B2 | 12/2007 | Huang et al. |
| 7,399,753 B2 | 7/2008 | Mitchell et al. |
| 7,462,354 B2 | 12/2008 | Sette et al. |
| 7,790,696 B2 | 9/2010 | Gregoriadis |
| 8,140,270 B2 | 3/2012 | Kingsmore et al. |
| 8,217,016 B2 * | 7/2012 | Hoerr ................ A61P 35/00 506/9 |
| 8,349,558 B2 | 1/2013 | Fatho et al. |
| 8,691,966 B2 | 4/2014 | Kariko et al. |
| 8,703,142 B2 | 4/2014 | Diamond et al. |
| 8,853,283 B2 | 10/2014 | Platscher et al. |
| 8,877,206 B2 | 11/2014 | Chen et al. |
| 9,115,402 B2 | 8/2015 | Hacohen et al. |
| 9,476,055 B2 | 10/2016 | Sahin et al. |
| 10,106,800 B2 | 10/2018 | Sahin et al. |
| 11,135,312 B2 | 10/2021 | Von Der Mülbe et al. |
| 11,421,038 B2 | 8/2022 | Hoerr et al. |
| 11,779,659 B2 | 10/2023 | Sahin et al. |
| 2002/0025939 A1 * | 2/2002 | Iversen .............. A61K 39/0011 435/375 |
| 2003/0083272 A1 | 5/2003 | Wiederholt et al. |
| 2003/0157113 A1 * | 8/2003 | Terman .............. A61K 39/0011 435/346 |
| 2004/0132181 A1 * | 7/2004 | Mitchell ............ C12N 15/1086 435/325 |
| 2004/0209274 A2 | 10/2004 | Daly |
| 2004/0235175 A1 * | 11/2004 | Gaudernack ............ A61P 35/00 435/459 |
| 2005/0032730 A1 * | 2/2005 | Von Der Mulbe .......... A61K 39/001189 514/44 R |
| 2007/0025968 A1 | 2/2007 | Van Der Burg et al. |
| 2009/0055944 A1 | 2/2009 | Korman et al. |
| 2009/0093433 A1 | 4/2009 | Woolf et al. |
| 2009/0217401 A1 | 8/2009 | Korman et al. |
| 2010/0129877 A1 | 5/2010 | Sahin et al. |
| 2011/0143397 A1 | 6/2011 | Kariko et al. |

(Continued)

FOREIGN PATENT DOCUMENTS

| | | |
|---|---|---|
| EP | 0726319 A2 | 8/1996 |
| EP | 0839912 A1 | 5/1998 |

(Continued)

OTHER PUBLICATIONS

Elango et al in "Optimized transfection of mRNA transcribed from a d(A/T) 100 tail-containing vector" (Biochem. Biphys. Comm. vol. 330, pp. 958-966, published Mar. 19, 2005). (Year: 2005).*
Malone et al in "Cationic liposome-mediated RNA transfection" (PNAS 1989 vol. 86, pp. 6077-6081). (Year: 1989).*
Hess et al in (Cancer Immunol Immunother (2006 vol. 55: pp. 672-683, published online Aug. 2, 2005). (Year: 2005).*

(Continued)

*Primary Examiner* — Catherine S Hibbert
(74) *Attorney, Agent, or Firm* — Choate, Hall & Stewart LLP; Brenda Herschbach Jarrell; Beejan Asady

(57) ABSTRACT

It was the object of the present invention to provide RNA with increased stability and translation efficiency and means for obtaining such RNA. It should be possible to obtain increased grades of expression by using said RNA in gene therapy approaches.

30 Claims, 15 Drawing Sheets

Specification includes a Sequence Listing.

(56) References Cited

U.S. PATENT DOCUMENTS

| | | | |
|---|---|---|---|
| 2012/0237975 | A1 | 9/2012 | Schrum et al. |
| 2013/0115272 | A1 | 5/2013 | de Fougerolles et al. |
| 2013/0123481 | A1 | 5/2013 | de Fougerolles et al. |
| 2013/0156849 | A1 | 6/2013 | de Fougerolles et al. |
| 2013/0203115 | A1 | 8/2013 | Schrum et al. |
| 2013/0237593 | A1 | 9/2013 | de Fougerolles et al. |
| 2013/0237594 | A1 | 9/2013 | de Fougerolles et al. |
| 2013/0244278 | A1 | 9/2013 | de Fougerolles et al. |
| 2013/0244279 | A1 | 9/2013 | de Fougerolles et al. |
| 2013/0245106 | A1 | 9/2013 | de Fougerolles et al. |
| 2013/0245107 | A1 | 9/2013 | de Fougerolles et al. |
| 2013/0255281 | A1 | 10/2013 | Bray |
| 2013/0266640 | A1 | 10/2013 | de Fougerolles et al. |
| 2013/0274129 | A1 | 10/2013 | Katzen et al. |
| 2014/0010861 | A1 | 1/2014 | Bancel et al. |
| 2014/0147454 | A1 | 5/2014 | Chakraborty et al. |
| 2015/0017211 | A1 | 1/2015 | de Fougerolles et al. |
| 2015/0030576 | A1 | 1/2015 | Bancel |
| 2015/0167017 | A1 | 6/2015 | Roy et al. |
| 2017/0009244 | A1 | 1/2017 | Sahin et al. |

FOREIGN PATENT DOCUMENTS

| | | | | |
|---|---|---|---|---|
| EP | | 1242108 | A1 | 9/2002 |
| EP | | 1361277 | A1 | 11/2003 |
| EP | | 2569633 | A2 | 3/2013 |
| EP | | 3230458 | A1 | 10/2017 |
| EP | | 3167059 | B1 | 6/2019 |
| WO | WO-1994/023031 | | A1 | 10/1994 |
| WO | WO-1998/014464 | | A1 | 4/1998 |
| WO | WO-1999/14346 | | A2 | 3/1999 |
| WO | WO-1999/020766 | | A2 | 4/1999 |
| WO | WO-1999/024566 | | A1 | 5/1999 |
| WO | WO-1999/052503 | | A2 | 10/1999 |
| WO | WO-2000/20029 | | A1 | 4/2000 |
| WO | WO-2000/067761 | | A1 | 11/2000 |
| WO | WO-2001/047959 | | A2 | 7/2001 |
| WO | WO-2001/093902 | | A2 | 12/2001 |
| WO | WO-2002/048377 | | A2 | 6/2002 |
| WO | WO-2002/083714 | | A2 | 10/2002 |
| WO | WO-02098443 | | A2 * | 12/2002 ......... A61K 38/1735 |
| WO | WO-2003/051401 | | A2 | 6/2003 |
| WO | WO-2003/068257 | | A1 | 8/2003 |
| WO | WO-2003/106692 | | A2 | 12/2003 |
| WO | WO-2004/004743 | | A1 | 1/2004 |
| WO | WO-2005/030250 | | A2 | 4/2005 |
| WO | WO-2005/039533 | | A1 | 5/2005 |
| WO | WO-2005/040816 | | A1 | 5/2005 |
| WO | WO-2005075644 | | A2 * | 8/2005 ............ C12N 15/67 |
| WO | WO-2005/110338 | | A2 | 11/2005 |
| WO | WO-2006/121168 | | A1 | 11/2006 |
| WO | WO-2007/024708 | | A2 | 3/2007 |
| WO | WO-2007/025760 | | A2 | 3/2007 |
| WO | WO-2007/031222 | | A2 | 3/2007 |
| WO | WO-2007/101227 | | A2 | 9/2007 |
| WO | WO-2008/080468 | | A1 | 7/2008 |
| WO | WO-2008/083174 | | A2 | 7/2008 |
| WO | WO-2008/085562 | | A2 | 7/2008 |
| WO | WO-2008/116078 | | A2 | 9/2008 |
| WO | WO-2008/156712 | | A1 | 12/2008 |
| WO | WO-2009/053041 | | A2 | 4/2009 |
| WO | WO-2009/118296 | | A2 | 10/2009 |
| WO | WO-2009/129227 | | A1 | 10/2009 |
| WO | WO-2010/066418 | | A1 | 6/2010 |
| WO | WO-2011/012316 | | A2 | 2/2011 |
| WO | WO-2011/143656 | | A2 | 11/2011 |
| WO | WO-2012/019168 | | A2 | 2/2012 |
| WO | WO-2012/045075 | | A1 | 4/2012 |
| WO | WO-2012/045082 | | A2 | 4/2012 |
| WO | WO-2012/135805 | | A2 | 10/2012 |
| WO | WO-2012/159729 | | A1 | 11/2012 |
| WO | WO-2013/040142 | | A2 | 3/2013 |
| WO | WO-2013/052523 | | A1 | 4/2013 |
| WO | WO-2013/090648 | | A1 | 6/2013 |
| WO | WO-2013/120628 | | A1 | 8/2013 |
| WO | WO-2013/124701 | | A2 | 8/2013 |
| WO | WO-2013/151663 | | A1 | 10/2013 |
| WO | WO-2013/151664 | | A1 | 10/2013 |
| WO | WO-2013/151665 | | A2 | 10/2013 |
| WO | WO-2013/151672 | | A2 | 10/2013 |
| WO | WO-2014/012051 | | A1 | 1/2014 |
| WO | WO-2014/071219 | | A1 | 5/2014 |
| WO | WO-2014/093924 | | A1 | 6/2014 |
| WO | WO-2014/144039 | | A1 | 9/2014 |
| WO | WO-2014/144711 | | A1 | 9/2014 |
| WO | WO-2014/144767 | | A1 | 9/2014 |
| WO | WO-2014/152027 | | A1 | 9/2014 |
| WO | WO-2014/152030 | | A1 | 9/2014 |
| WO | WO-2014/152031 | | A1 | 9/2014 |
| WO | WO-2014/152211 | | A1 | 9/2014 |
| WO | WO-2014/159813 | | A1 | 10/2014 |
| WO | WO-2014/160243 | | A1 | 10/2014 |
| WO | WO-2014/164253 | | A1 | 10/2014 |
| WO | WO-2014/168874 | | A2 | 10/2014 |
| WO | WO-2015/014375 | | A1 | 2/2015 |
| WO | WO-2015/034925 | | A1 | 3/2015 |
| WO | WO-2015/034928 | | A1 | 3/2015 |
| WO | WO-2015/038892 | | A1 | 3/2015 |
| WO | WO-2015/043613 | | A1 | 4/2015 |
| WO | WO-2015/051169 | | A2 | 4/2015 |
| WO | WO-2015/051173 | | A2 | 4/2015 |
| WO | WO-2015/058780 | | A1 | 4/2015 |
| WO | WO-2015/085318 | | A2 | 6/2015 |
| WO | WO-2015/089511 | | A2 | 6/2015 |
| WO | WO-2015/117620 | | A1 | 8/2015 |
| WO | WO-2015/164674 | | A1 | 10/2015 |
| WO | WO-2015/172843 | | A1 | 11/2015 |
| WO | WO-2016/005004 | | A1 | 1/2016 |
| WO | WO-2016/005324 | | A1 | 1/2016 |
| WO | WO-2016/062323 | | A1 | 4/2016 |
| WO | WO-2016/091391 | | A1 | 6/2016 |
| WO | WO-2016/107877 | | A1 | 7/2016 |
| WO | WO-2016/155809 | | A1 | 10/2016 |

OTHER PUBLICATIONS

Caruso et al (published online Feb. 3, 2005): (Year: 2005).*
Hunziker et al (Virology 2004 vol. 330, pp. 196-208). (Year: 2004).*
Heiser et al in "Human dendritic cells transfected with RNA encoding prostate-specific antigen stimulate prostate-specific CTL responses in vitro." (J. Immunol. 2000, vol. 164, pp. 5508-5514; IDS ref). (Year: 2000).*
Heiser et al in "Autologous dendritic cells transfected with prostate-specific antigen RNA stimulate CTL responses against metastatic prostate tumors" J. Clin. Invest. 2002, vol. 109, pp. 409-417; IDS ref). (Year: 2002).*
Xue et al (Infection And Immunity, Nov. 2004, pp. 6324-6329): (Year: 2004).*
Lingna Wang Dissertation U of Texas Aug. 2005 (Year: 2005).*
Castagnetti & Ephrussi in "Orb and a long poly(A) tail are required for efficient oskar translation at the posterior pole of the *Drosophila* oocyte" (Development 130, pp. 835-843). (Year: 2003).
Passmore et al (Nature Reviews vol. 23, 2022; pp. 93-106) (Year: 2021).
Agrawal et al., Trend in Biotechnology, 14(10): 376-387, 1996.
Bargmann, C.I., Hung, M.C., and Weinberg, R.A. The neu oncogene encodes an epidermal growth factor receptor-related protein. Nature 319, 226-230 (1986).
Beckel-Mitchener, A. C., et al., Poly(A) tail length-dependent stabilization of GAP-43 mRNA by the RNA-binding protein HuD, Journal of Biological Chemistry, 277(31):27996-28002, (2002).
Bei et al.J Immunother. May 1998;21(3):159-69.
Boczkowski et al. (1996). Dendritic cells pulsed with RNA are potent antigen-presenting cells in vitro and in vivo, J Exp. Med. 184: 465-472.
Boczkowski, D., Nair, S.K., Nam, J.H., Lyerly H.K., and Gilboa, E. (2000). Induction of tumor immunity and cytotoxic T lymphocyte responses using dendritic cells transfected with messenger RNA amplified from tumor cells. Cancer Res. 60, 1028-1034.

(56) References Cited

OTHER PUBLICATIONS

Bowerman, NA. "Engineering the binding properties of the T cell receptor: peptide: MHC ternary complex that governs T cell activity." Mol. Immun. 46: 3000-3008, 2009.
Brickner et al. J Exp. Med 193(2) 195-205 (2001).
Carralot, J.P., Probst, J., Hoerr, I., Scheel, B., Teufel, R., Jung, G., Rammensee, H.G., and Pascolo, S. (2004). Polarization of immunity induced by direct injection of naked sequence-stabilized mRNA vaccines. Cell Mol. Life Sci. 61, 2418-2424.
Carrazana E. J., et al., The vasopressin mRNA poly(A) tract is unusually long and increases during stimulation of vasopressin gene expression in vivo, Mol & Cell Biol, 8(6):2267-2274, (1988).
Cloning vector pGL3 Promoter, downloaded Jan. 16, 2021, 3 pages.
Condon, C., Watkins, S.C., Celluzzi, C.M., Thompson, K., and Falo, L.D., Jr. (1996). DNA-based immunization by in vivo transfections of dendritic cells. Nat. Med. 2, 1122-1128.
Conry et al. (1995). Characterization of a messenger RNA polynucleotide vaccine vector, Cancer Res. 55: 1397-1400.
Conry, R.M., LoBuglio, A.F., Kantor, J., Schlom, J., Loechel, F., Moore, S.E., Sumerel, L.A., Barlow, D.L., Abrams, S., and Curiel, D.T. (1994). Immune response to a carcinoembryonic antigen polynucleotide vaccine. Cancer Res. 54, 1164-1168.
Conry, R.M., LoBuglio, A.F., Loechel, F., Moore, S.E., Sumerel, L.A., Barlow, D.L., and Curiel, D.T. (1995a). A carcinoembryonic antigen polynucleotide vaccine has in vivo antitumor activity. Gene Ther. 2, 59-65.
Conry, R.M., LoBuglio, A.F., Wright, M., Sumerel, L., Pike, M.J., Johanning, F., Benjamin, R., Lu, D., and Curiel, D.T. (1995b). Characterization of a messenger RNA polynucleotide vaccine vector. Cancer Res. 55, 1397-1400.
Coulie et al. (1995). A mutated intron sequence codes for an antigenic peptide recognized by cytolytic T lymphocytes on a human melanoma, Proc. Natl. Acad. Sci. USA 92: 7976-7980.
Cox, G.J., Zamb, T.J., and Babiuk, L.A. (1993). Bovine herpesvirus 1: immune responses in mice and cattle injected with plasmid DNA. J. Virol. 67, 5664-5667.
Davis, H.L., Michel, M.L., and Whalen, R.G. (1993). DNA-based immunization induces continuous secretion of hepatitis B surface antigen and high levels of circulating antibody. Hum. Mol. Genet. 2, 1847-1851.
Del Val et al., Cell, vol. 66, Issue 6, Sep. 20, 1991, pp. 1145-1153.
Dengjel, J et al. Glycan side chains on naturally presented MHC class II ligands J Mass Spectrom, 2005.
Ding et al. Genome remodeling in a basal-like breast cancer metastasis and xenograft Nature, 464: 999-1005, 2010.
Dolgin, "The Billion-Dollar Biotech," Nature, vol. 522, pp. 26-28, Jun. 4, 2015.
Edmonds, "Progress in Nucleic Acid Research and Molecular Biology", (2002), vol. 71, p. 285-389.
Elango, N. et al., Optimized transfection of mRNA transcribed from a d(A/T) 100 tail-containing vector, Biochem Biophys Res Commun., 330(3):958-66 (2005).
Fritsch, E. F. et al. HLA-Binding Properties of Tumor Neoepitopes in Humans Cancer Immunology Research, 2: 522-529, 2014.
Gallie et al. Mol Gen Genet (1991) 228:258-264.
Gallie, "A tale of two termini: A functional interaction between termini of an mRNA is a prerequisite for efficient translation initiation", Gene, Elsevier 1-11 (1998).
Gallie, D.R. (1991). The cap and poly(A) tail function synergistically to regulate mRNA translational efficiency. Genes Dev. 5, 2108-2116.
Gilkeson, G.S., Pippen, A.M., and Pisetsky, D.S. (1995). Induction of cross-reactive anti-dsDNA antibodies in preautoimmune NZB/NZW mice by immunization with bacterial DNA. J. Clin. Invest. 95, 1398-1402.
Gnirke, A. Solution hybrid selection with ultra-long oligonucleotides for massively parallel targeted sequencing Nat. Biotechnol, 2009.
Goya, R. et al. SNVMix: predicting single nucleotide variants from next-generation sequencing of tumors, Bioinformatics Bioinformatics, 26: 730-736, 2010.
Greenblatt, M.S., Bennett, W.P., Hollstein, M., and Harris, C.C. (1994). Mutations in the p53 tumor suppressor gene: clues to cancer etiology and molecular pathogenesis. Cancer Res. 54, 4855-4878.
Gryaznov et al., Biochim. Biophys. Acta, 1489: 131-140, 1999.
Guhaniyogi et al., "Regulation of mRNA stability in mammalian cells", Gene, Elsevier, 11-23 (2001).
Guyre et al., Cancer Immunother (1997) 45:146-148.
Hacohen Decl. dated Feb. 16, 2014 filed in U.S. Appl. No. 13/108,610, 10 pages.
Heiser, A., Coleman, D., Dannull, J., Yancey, D., Maurice, M.A., Lallas, C.D., Dahm, P., Niedzwiecki, D., Gilboa, E., and Vieweg, J. (2002). Autologous dendritic cells transfected with prostate-specific antigen RNA stimulate CTL responses against metastatic prostate tumors. J. Clin. Invest 109, 409-417.
Heiser, A., Dahm, P., Yancey, D.R., Maurice, M.A., Boczkowski, D., Nair, S.K., Gilboa, E., and Vieweg, J. (2000). Human dendritic cells transfected with RNA encoding prostate-specific antigen stimulate prostate-specific CTL responses in vitro. J. Immunol. 164, 5508-5514.
Hoerr, I., Obst, R., Rammensee, H.G., and Jung, G. (2000). In vivo application of RNA leads to induction of specific cytotoxic T lymphocytes and antibodies. Eur. J. Immunol. 30, 1-7.
Holtkamp et al., Gene Therapy: prepublished online as Blood First Edition Paper, pp. 3009-4017, (2006).
Holtkamp, Silke, et al., "Modification of Antigen-Encoding RNA Increases Stability, Translational Efficacy, and T-Cell Stimulatory Capacity of Dendritic Cells," Blood, vol. 108, No. 13. (2006).
International Preliminary Report on Patentability Chapter I, Dated Apr. 1, 2008, Filed in relation to PCT Application No. PCT/EP2006/009448, Filed Apr. 5, 2007, Entitled "Modification of RNA, Producing an Increased Transcript Stability and Translation Efficiency," By Applicant "Johannes Gutenberguniversitat Mainz, Vertreten Durch Den Pra.Sidenten," 9 pages.
International Search Report (ISR), Dated May 8, 2007, Filed in relation to PCT Application No. PCT/EP2006/009448, Filed Apr. 5, 2007, Entitled "Modification of RNA, Producing an Increased Transcript Stability and Translation Efficiency," By Applicant "Johannes Gutenberg-Universitat Mainz, Vertreten Durch Den Pra.Sidenten," 15 pages.
Johanning et al. Nucleic Acids Res. May 11, 1995; 23(9): 1495-1501.
Kenter, G. G. et al. "Phase I Immunotherapeutic Trial with Long Peptides Spanning the E6 and E7 sequences of High-risk human papillomavirus 16 in End-stage cervical cancer patients shows low toxicity and robust immunogenicity." Clinical Cancer Research, 14: 169-177, 2008.
Keogh, E. et al. "Identification of New Epitopes from Four Different Tumor-Associated Antigens: Recognition of Naturally Processed Epitopes Correlates with HLA-A*0201-Binding Affinity" J. Immunol. 167: 787-796, 2001.
Krieg & Melton, vol. 12 No. 18 (1984) Nucleic Acids Research.
Lemmel, Claudia et al., Differential quantitative analysis of MHC ligands by mass spectrometry using stable isotope labeling Nat Biotechnol, 2004.
Lennerz et al. (2005). The response of autologous T cells to a human melanoma is dominated by mutated neoantigens, Proc. Natl. Acad. Sci. USA 102: 16013-16018.
Ley et al. (2008). DNA sequencing of a cytogenetically normal acute myeloid leukaemia genome, Nature 456: 66-72.
Li et al., Cancer Genome Sequencing and Its Implications for Personalized Cancer Vaccine, Cancer 2011, 3, 4191-4211.
Li, X., et al., "Generation of Destabilized Green Fluorescent Protein as a Transcription Reporter," Journal of Biological Chemistry, 273(52):34970-34975 (1998).
Maksyutov and Zagrebelnaya (1993). ADEPT: a computer program for prediction of protein antigenic determinants, Comput. Appl. Biosci. 9: 291-297.
Malone, R.W., Felgner, P.L., and Verma, I.M. (1989). Cationic liposome-mediated RNA transfection. Proc. Natl. Acad. Sci. USA 86, 6077-6081.

(56) References Cited

OTHER PUBLICATIONS

Mandelboim et al. (1995). Regression of established murine carcinoma metastases following vaccination with tumour-associated antigen peptides, Nature Medicine 1: 1179-1183.
Mardis, ER., Recurring Mutations Found by Sequencing an Acute Myeloid Leukemia Genome, New England J. Med., 361:1058-1066 (2009).
Margulies, Marcel et al., Genome Sequencing in Open Microfabricated High Density Picoliter Reactors Nature, 2005.
Martinon et al. (1993). Induction of virus-specific cytotoxic T lymphocytes in vivo by liposome-entrapped mRNA. Eur. J. Immunol 23, 1719-1722.
Mayer et al., Anticancer Research 25:3917-3924 (2005).
Meyerson, M. et al. Advances in understanding cancer genomes through second-generation sequencing Nature Rev. Genetics. 11:685-695, 2010.
Mignone, F., et al., "Untranslated Regions of mRNAs," Genome Biology, vol. 3, No. 3. (2002).
Monach et al. (1995). A unique tumor antigen produced by a single amino acid substitution, Immunity 2: 45-59.
Mortazavi (2008). Mapping and quantifying mammalian transcriptomes by RNA-Seq, Nature Methods 5: 621-628.
Parker et al., J. Immunol. 152 (1994), 163-175.
Parkhurst, MR. et al. "Improved Induction of Melanoma-reactive CTL with peptides from the melanoma antigen gp100 modified at HLA-A*0201-binding residues." J. Immunol. 157: 2549-2548, 1996.
Parmiani, G. et al. "Unique Human Tumor Antigens: Immunobiology and Use in Clinical Trials." The Journal of Immunology, 178: 1975-1979, 2007.
PBluescript II KS Sequence and Map, downloaded Jan. 16, 2021, 11 pages.
Peak, I. and Axel, R., Glucocorticoids enhance stability of human growth hormone mRNA, Mol & Cell Biol., 7(4):1496-1507, (1987).
Perissi et al., Electron Spin Resonance and Differential Scanning Calorimetry as Combined Tools for the Study of Liposomes in the Presence of Long Chain Nitroxides, 106 J_ of Phys. Chem. B 10468 (2002).
Pesole, G., et al., "Structural and Functional Features of Eukaryotic mRNA Untranslated Regions," Gene: An International Journal on Genes and Genomes, vol. 276, No. 1-2, (2001).
Pfohl et al., Biological Polyelectrolyte Complexes in Solution and Confined on Patterned Surfaces, 198-200 Colloids & Surfaces A: Physicochemical and Eng. Aspects 613 (2002).
PGL3 Luciferase Reporter Vectors, downloaded Jan. 16, 2021, 3 pages.
Pilla, L. et al. Multipeptide vaccination in cancer patients Expert Opinion on Biological Therapy, 9: 1043-1055, 2009.
Pleasance, E. et al. A small-cell lung cancer genome with complex signatures of tobacco exposure. Nature, 463: 184-190, 2010.
Pleasance, E. et al., A comprehensive catalogue of somatic mutations from a human cancer genome, Nature, 463:191-196 (2010).
Preiss, T. and Hentze, M.W. (1998). Dual function of the messenger RNA cap structure in poly(A)-tail promoted translation in yeast. Nature 392, 516-520.
Proudfoot, Nicholas J., Cell, vol. 10, 559-570. Apr. 1977.
Rabinovich, P. et al., Synthetic Messenger RNA as a Tool for Gene Therapy, Human Gene Therapy, 17:1027-1-35 (2006).
Rammansee 2008, Chapter 50: Cancer Vaccines: Some Basic Considerations, Genomic and Personalized Medicine, Hungtington and Ginsburg. E-published on Nov. 11, 2008.
Rammensee (2006). "Some considerations on the use of peptides and mRNA for therapeutic vaccination against cancer," Immunol Cell Biol. 84(3):290-4.
Rammensee et al. (2002). "Toward patient-specific tumor antigen selection for vaccination," Immunol. Rev. 188: 164-176.
Rammensee et al., Immunogenentics, 50 (1999), 213-219.
Rao (1994). "Epitope-based vaccines: One step at a time," Proc. Indian natn. Sci. Acad. B60: 419-424.
Ressing, M. et al. "Human CTL epitopes encoded by human papillomavirus types 16 E6 and E7 identified through in vivo and in vitro immunogenicity studies of HLA-A*0201-binding peptides" J. Immunol. 154:5934-5943, 1995.
Richter Joel D: "Cytoplasmic polyadenylation in development and beyond", Jun. 1999, Microbiology and Molecular Biology Reviews, vol. 63, NR. 2, pp. 446-456, XP002641650.
Russell and Liebhaber in "The stability of human beta-globin mRNA is dependent on structural determinants positioned within its 3' untranslated region"(Blood Journal: 1996, vol. 87: pp. 5314-5323).
Russell, J. and Liebhaber, S., The stability of human beta-globin mRNA is dependent on structural determinants positioned within its 3' untranslated region, Blood, 87(12):5314-23 (1996).
Saenz-Badillos et al. (2001). RNA as a tumor vaccine: a review of the literature, Exp Dermatol. 10(3):143-54.
Segal et al. (2008). Epitope landscape in breast and colorectal cancer, Cancer Res. 68: 889-892.
Sensi and Aanichini, Unique Tumor Antigens: Evidence for Immune Control of Genome Integrity and Immunogenic Targets for T cell-mediated Patient-Specific Immunotherapy, Clin. Cancer Res. 2006:12(17), 5023.
Sette, A. et al. "Peptide Binding to the Most Frequent HLA-A Class I Alleles Measured by Quantitative Molecular Binding Assays" Mol. Immunol. 31: 813-822, 1994.
Sette, A. et al. "The Relationship Between Class I Binding Affinity and Immunogenicity of Potential Cytotoxic T cell Epitopes." J. Immunol. 153: 5586-5592, 1994.
Shah et al. (2009). Mutation of FOXL2 in granulosa-cell tumors of the ovary, N. Eng. J Med. 360: 2719-2729.
Sjoblom et al. (2006). The consensus coding sequences of human breast and colorectal cancers, Science 314: 268-274.
Spooner, R.A., Deonarain, M.P., and Epenetos, A.A. (1995). DNA vaccination for cancer treatment. Gene Ther. 2, 173-180.
Stephens et al. (2005). "A screen of the complete protein kinase gene family identities diverse patterns of somatic mutations in human breast cancer," Nature Genetics, 37: 590-592.
Strong, T.V., Hampton, T.A., Louro, I., Bilbao, G., Conry, R.M., and Curiel, D.T. (1997). Incorporation of beta-globin untranslated regions into a Sindbis virus vector for augmentation of heterologous mRNA expression. Gene Ther. 4, 624-627.
Su, Z., Dannull, J., Heiser, A., Yancey, D., Pruitt, S., Madden, J., Coleman, D., Niedzwiecki, D., Gilboa, E., and Vieweg, J. (2003). Immunological and clinical responses in metastatic renal cancer patients vaccinated with tumor RNA-transfected dendritic cells. Cancer Res. 63, 2127-2133.
Tang, D.C., DeVit, M., and Johnston, S.A. (1992). Genetic immunization is a simple method for eliciting an immune response. Nature 356, 152-154.
Tanguay et al., "Translational efficiency is regulated by the length of the 3' untranslated region", Molecular and Cellular Biology, American Society for Microbiology, 146-156 (1996).
Teufel, R., Carralot, J.P., Scheel, B., Probst, J., Walter, S., Jung, G., Hoerr, I., Rammensee, H.G., and Pascolo, S. (2005). Human peripheral blood mononuclear cells transfected with messenger RNA stimulate antigen-specific cytotoxic T-lymphocytes in vitro. Cell Mol. Life Sci. 62, 1755-1762.
ThermoFisher Esp3l (BsmBI) datasheet, downloaded Jan. 16, 2021, 4 pages.
Thomson et al., J Virology (1998), 72(3):2246-2252.
Toes et al. (1997). Protective anti-tumor immunity induced by vaccination with recombinant adenoviruses encoding multiple tumor-associated cytotoxic T lymphocyte epitopes in a string- of-beads fashion, Proc. Natl. Acad. Sci. USA 94:14660-14665.
Ulmer, J.B., Donnelly, J.J., Parker, S.E., Rhodes, G.H., Feigner, P.L., Dwarki, V.J., Gromskowski, S.H., Deck, R.R., DeWitt, C.M., Friedman, A., et al. (1993). Heterologous protection against influenza by injection of DNA encoding a viral protein. Science 259, 1745-1749.
UniProtKB—P36888 (FLT3_HUMAN), last sequence update: Aug. 21, 2007.
UniProtKB—Q5SW79 (CE170_HUMAN), last sequence update: Dec. 21, 2004.

(56) References Cited

OTHER PUBLICATIONS

UniProtKB—Q9NVD7 (Parva_Human), last sequence update: Oct. 1, 2000.
UniProtKB, "Print-outs from the UniProtKB database concerning the CEP170, Parva and FLT3 genes."
Van der Bruggen et al. (1991). A gene encoding an antigen recognized by cytolytic T lymphocytes on a human melanoma, Science 254: 1643-1647.
Van Laere AS, Nguyen M, Braunschweig M. et al. A regulatory mutation in IGF2 causes a major QTL effect on muscle growth in the pig. Nature. 2003;425(6960):832-836.
Vioque, et al. J. Mol. Biol., (1988), vol. 202, p. 835-848.
Wang, B., Merva, M., Dang, K., Ugen, K.E., Williams, W.V., and Weiner, D.B. (1995). Immunization by direct DNA inoculation induces rejection of tumor cell challenge. Hum. Gene Ther. 6, 407-418.
Wang, B., Ugen, K.E., Srikantan, V., Agadjanyan, M.G., Dang, K., Refaeli, Y., Sato, A.I., Boyer, J., Williams, W.V., and Weiner, D.B. (1993). Gene inoculation generates immune responses against human immunodeficiency virus type 1. Proc. Natl. Acad. Sci. USA 90, 4156-4160.
Weinschenk et al. (2002), Integrated functional genomics approach for the design of patient-individual antitumor vaccines, Cancer Res 62: 5818-5827.
Wickens M et al: "A PUF family portrait: 3'UTR regulation as a way of life", Trends in Genetics, Elsevier Science Publishers B.V. Amsterdam, NL, vol. 18, nr. 3, Mar. 1, 2002, pp. 150-157, XP004340609.
Wolff, J.A., Malone, R.W., Williams, P., Chong, W., Acsadi, G., Jani, A., and Feigner, P.L. (1990). Direct gene transfer into mouse muscle in vivo. Science 247, 1465-1468.
Wood et al. (2007). The genomic landscapes of human breast and colorectal cancers, Science 318: 1108-1113.
Wortzel et al. (1983). Multiple tumour-specific antigens expressed on a single tumour cell, Nature 304: 165-167.
Written Opinion of the International Search Authority, Dated May 8, 2007, Filed in relation to PCT Application No. PCT/EP2006/009448, Filed Apr. 5, 2007, Entitled "Modification of Rna, Producing an Increased Transcript Stability and Translation Efficiency," By Applicant "Johannes Gutenberguniversitat Mainz, Vertreten Durch Den Pra.Sidenten," 8 pages.

Ying, H., Zaks, T.Z., Wang, R.F., Irvine, K.R., Kammula, U.S., Marincola, F.M., Leitner, W.W., and Restifo, N.P. (1999). Cancer therapy using a self-replicating RNA vaccine. Nat. Med. 5, 823-827.
Yu. Jia, et al., Structural and Functional Analysis of an mRNP Complex that Mediates the High Stability of Human Beta-globulin mRNA, Molecular and Cellular Biology, Vo. 21, No. 17. (2001).
Zhou et al., Hum. Gene Ther., 10(16):2719-24, 1999.
Sachs, A., The role of poly(A) in the translation and stability of mRNA, Curr Opin Cell Biol., 2(6):1092-8 (1990).
Khanam, T. et al., Poly(A)-binding protein binds to A-rich sequences via RNA-binding domains 1+2 and 3+4, RNA Biol., 3(4):170-7 (2006).
Milone, J. et al., Characterization of deadenylation in trypanosome extracts and its inhibition by poly(A)-binding protein Pab1p, RNA, 10(3):448-57 (2004).
Chen, CY and Shyu, AB, AU-rich elements: characterization and importance in mRNA degradation, Trends Biochem Sci., 20(11):465-70 (1995).
Gallie, DR. et al., The histone 3'-terminal stem-loop is necessary for translation in Chinese hamster ovary cells, Nucleic Acids Res., 24(10):1954-62 (1996).
Zhao, Y. et al., Multiple injections of electroporated autologous T cells expressing a chimeric antigen receptor mediate regression of human disseminated tumor, Cancer Res., 70(22):9053-61 (2010).
Pandey, NB and Marzluff, WF, The stem-loop structure at the 3' end of histone mRNA is necessary and sufficient for regulation of histone mRNA stability, Mol Cell Biol., 7(12):4557-9 (1987).
Bernstein, P. et al., The poly(A)-poly(A)-binding protein complex is a major determinant of mRNA stability in vitro, Mol Cell Biol., 9(2):659-70 (1989).
Trepotec, Z. et al., Segmented poly(A) tails significantly reduce recombination of plasmid DNA without affecting mRNA translation efficiency or half-life, RNA, 25(4):507-518 (2019).
Leppek, K. et al., Combinatorial optimization of mRNA structure, stability, and translation for RNA-based therapeutics, Nat Commun., 13(1):1536 (2022).
Dubensky, TW, Jr. et al., Sindbis virus DNA-based expression vectors: utility for in vitro and in vivo gene transfer, J Virol., 70(1):508-19 (1996).
Tarun, S. et al., Deardorff JA, Sachs AB. Translation initiation factor eIF4G mediates in vitro poly(A) tail-dependent translation, Proc Natl Acad Sci USA, 94(17):9046-51 (1997).

* cited by examiner

Vector Constructs

Vector Constructs

IVT vectors          mRNA transcripts pGEM3Z-eGFP-A120-SapI pGEM3Z-eGFP-1BgUTR-A120-SapI pGEM3Z-eGFP-2BgUTR-A120-SapI pST1-Sec-SIINFEKL-2BgUTR-A120-SapI pST1-Sec-SIINFEKL-2BgUTR-A120-SpeI pST1-eGFP-A67-SpeI pST1-Sec-SIINFEKL-A67-SpeI pST1-Sec-pp65-2BgUTR-A120-SapI pST1-Sec-pp65-A67-SpeI

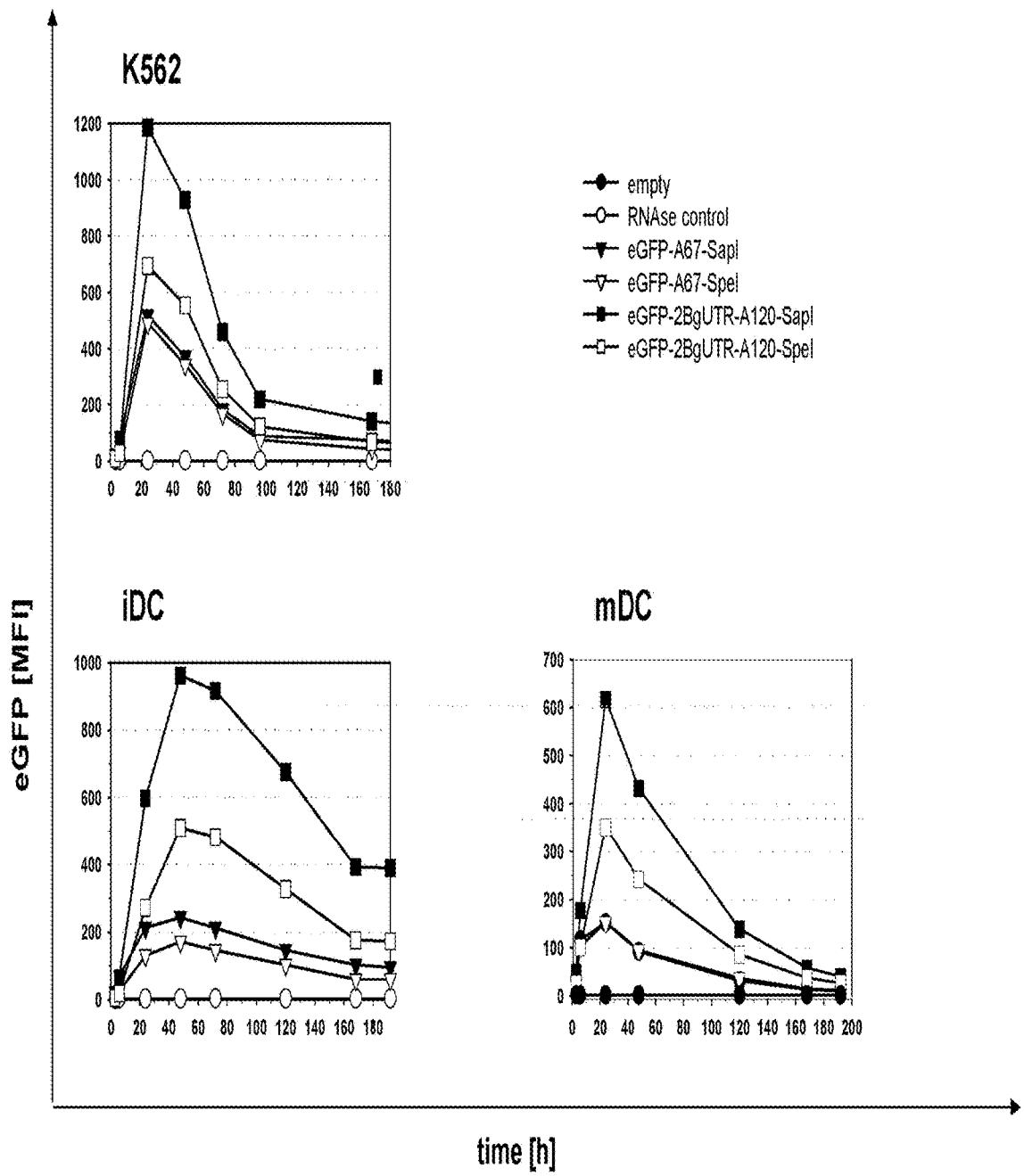

MODIFICATION OF RNA, PRODUCING AN INCREASED TRANSCRIPT STABILITY AND TRANSLATION EFFICIENCY

This application is a Division of U.S. patent application Ser. No. 16/143,520 filed Sep. 27, 2018, which is a Continuation of U.S. patent application Ser. No. 15/217,555 filed Jul. 22, 2016 (issued as U.S. Pat. No. 10,106,800), which is a Division of U.S. patent application Ser. No. 11/992,638 filed Aug. 14, 2009 (issued as U.S. Pat. No. 9,476,055), which is a U.S. National Stage Application submitted under 35 U.S.C. 371 of International Application Serial Number PCT/EP2006/009448, filed on Sep. 28, 2006, which claims priority to German Application Serial No. 102005046490.4, filed Sep. 28, 2005. The entire content of each of the above-referenced Applications are incorporated herein by reference.

SEQUENCE LISTING

The instant application contains a Sequence Listing which has been submitted electronically in XML format and is hereby incorporated by reference in its entirety. Said XML copy, created on Oct. 21, 2022, is named 2013237-0364_SL.xml and is 10,545 bytes in size.

BACKGROUND

Conventional vaccines, including attenuated or inactivated pathogens, are effective in many areas but nevertheless do not impart effective protective immunity to some infectious pathogens and tumors. This requires vaccines which are effective, versatile, ready and cost-effective to produce and easy to store.

After direct intramuscular injection of plasmid DNA had been shown to result in prolonged expression of the coded genes on the cell surface (Wolff et al., 1990), DNA-based vaccines were regarded as a new promising immunization strategy. This provided an important incentive for developing vaccines based on nucleic acids. Initially, DNA-based vaccines to infectious pathogens were tested (Cox et al., 1993; Davis et al., 1993; Ulmer et al., 1993; Wang et al., 1993) but were soon however researched in more detail also in gene therapy against tumors in order to induce specific antitumor immunity (Conry et al., 1994; Conry et al., 1995a; Spooner et al., 1995; Wang et al., 1995). This strategy of tumor immunization has a number of important advantages. Vaccines based on nucleic acids are easy to prepare and relatively inexpensive. They may moreover be amplified from a small number of cells.

DNA is more stable than RNA but carries some potential safety risks such as the induction of anti-DNA antibodies (Gilkeson et al., 1995) and integration of the transgene into the host genome. This may inactivate cellular genes, cause uncontrollable long term expression of said transgene or oncogenesis and is therefore usually not applicable to tumor-associated antigens with oncogenic potential, such as, for example, erb-B2 (Bargmann et al., 1986) and p53 (Greenblatt et al., 1994). The use of RNA offers an attractive alternative in order to circumvent these potential risks.

The advantages of using RNA as a kind of reversible gene therapy include transient expression and a non-transforming character. The RNA does not need to enter the nucleus in order to be expressed transgenically and moreover cannot integrate into the host genome, thereby eliminating the risk of oncogenesis. As with DNA (Condon et al., 1996; Tang et al., 1992), injection of RNA can also induce both the cellular and humoral immune responses in vivo (Hoerr et al., 2000; Ying et al., 1999).

The immune therapy with in vitro-transcribed RNA (IVT-RNA) makes use of two different strategies both of which have been successively tested in various animal models. Either RNA is directly injected via different routes of immunization (Hoerr et al., 2000) or dendritic cells (DCs) are transfected with in vitro-transcribed RNA by means of lipofection or electroporation and administered thereafter (Heiser et al., 2000). Recently published studies demonstrated that immunization with RNA-transfected DCs induces antigen-specific cytotoxic T lymphocytes (CTL) in vitro and in vivo (Su et al., 2003; Heiser et al., 2002). A factor of central importance for optimal induction of the T cell-mediated immune responses is inter alia the dose, i.e. density of antigen presentation on the DCs. It has been attempted to stabilize IVT-RNA by various modifications in order to achieve prolonged expression of transferred IVT-RNA and thereby to increase antigen presentation on DCs. A basic requirement for translation is the presence of a 3' poly(A) sequence, with the translation efficiency correlating with the length of poly(A) (Preiss and Hentze, 1998). The 5' cap and 3' poly(A) sequence synergistically activate translation in vivo (Gallie, 1991). Untranslated regions (UTRs) of globin genes are other known elements which can contribute to stabilizing RNA and increasing translation efficiency (Malone et al., 1989).

Some IVT vectors are known in the literature which are utilized in a standardized manner as template for in vitro transcription and which have been genetically modified in such a way that stabilized RNA transcripts are produced. Protocols currently described in the literature (Conry et al., 1995b; Teufel et al., 2005; Strong et al., 1997; Carralot et al., 2004; Boczkowski et al., 2000) are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

RNA therefore seems to be particularly suitable for clinical applications. However, the utilization of RNA in gene therapy is greatly restricted especially by the short half life of RNA, in particular in the cytoplasma, resulting in low protein expression.

BRIEF SUMMARY OF THE INVENTION

It was the object of the present invention to provide RNA with increased stability and translation efficiency and means for obtaining such RNA. It should be possible to obtain increased grades of expression by using said RNA in gene therapy approaches.

This object is achieved according to the invention by the subject matter of the claims.

The present invention relates to stabilization of RNA, in particular mRNA, and an increase in mRNA translation. The present invention particularly relates to three modifications of RNA, in particular in vitro-transcribed RNA, resulting in increased transcript stability and translation efficiency.

According to the invention, RNA having an open-ended poly(A) sequence was found to be translated more efficiently than RNA having a poly(A) sequence with a masked terminus. It was found that a long poly(A) sequence, in particular of about 120 bp, results in optimal RNA transcript stability and translation efficiency. The invention also demonstrated that a double 3'-untranslated region (UTR), in particular of the human beta-globin gene, in an RNA molecule improves translation efficiency in a way which clearly exceeds the total effect to be expected using two individual UTRs. A combination of the above-described modifications was found according to the invention to have a synergistic influence on the stabilization of RNA and the increase in translation.

Using quantitative RT-PCR and eGFP variants for measuring transcript quantities and protein yield, the invention demonstrated that the RNA modifications according to the invention independently enhance RNA stability and translation efficiency in the transfection of dendritic cells (DCs). Thus it was possible to increase the density of antigen-specific peptide/MHC complexes on the transfected cells and their ability to stimulate and expand antigen-specific $CD4^+$ and $CD8^+$ T cells. The invention therefore relates to a strategy for optimizing RNA-transfected DC vaccines by using RNA which has been modified by the RNA modifications described according to the invention.

According to the invention, modification, and thereby stabilization and/or increase in translation efficiency, of RNA is preferably achieved by genetically modifying expression vectors which preferably serve as template for RNA transcription in vitro.

Vectors of this kind are intended to allow in particular transcription of RNA with a poly(A) sequence which preferably has an open end in said RNA, i.e. no nucleotides other than A nucleotides flank said poly(A) sequence at its 3' end. An open-ended poly(A) sequence in the RNA can be achieved by introducing a type IIS restriction cleavage site into an expression vector which allows RNA to be transcribed under the control of a 5' RNA polymerase promoter and which contains a polyadenyl cassette (poly(A) sequence), wherein the recognition sequence is located 3' of the poly(A) sequence, while the cleavage site is located upstream and thus within the poly(A) sequence. Restriction cleavage at the type IIS restriction cleavage site enables a plasmid to be linearized within the poly(A) sequence (FIG. 2). The linearized plasmid can then be used as template for in vitro transcription, the resulting transcript ending in an unmasked poly(A) sequence.

Furthermore or alternatively, a modification, and thereby stabilization and/or increase in translation efficiency, of RNA can be achieved according to the invention by genetically modifying expression vectors in such a way that they allow transcription of RNA with two or more 3'-untranslated regions at its 3' end, and preferably between the sequence coding for a peptide or protein (open reading frame) and the poly(A) sequence.

In one aspect, the invention relates to a nucleic acid molecule comprising in the 5'→3' direction of transcription: (a) a promoter; (b) a transcribable nucleic acid sequence or a nucleic acid sequence for introducing a transcribable nucleic acid sequence; (c-1) a first nucleic acid sequence which corresponds to the 3'-untranslated region of a gene or is derived therefrom; and (c-2) a second nucleic acid sequence which corresponds to the 3'-untranslated region of a gene or is derived therefrom.

In one embodiment, the nucleic acid molecule according to the invention further comprises (c-3) at least one further nucleic acid sequence which corresponds to the 3'-untranslated region of a gene or is derived therefrom.

In the nucleic acid molecule according to the invention, the nucleic acid sequences (b), (c-1), (c-2) and, where appropriate, (c-3) under the control of the promoter (a) can preferably be transcribed to give a common transcript in which the nucleic acid sequences transcribed from the nucleic acid sequences (c-1) and/or (c-2) and/or, where appropriate, (c-3) are preferably active so as to increase the translation efficiency and/or the stability of the nucleic acid sequence transcribed from the transcribable nucleic acid sequence (b).

The nucleic acid sequences (c-1), (c-2) and, where appropriate, (c-3) may be identical or different.

In one embodiment, the nucleic acid molecule further comprises (d) a nucleic acid sequence which, when transcribed under the control of the promoter (a), codes for a nucleotide sequence of at least 20 consecutive A nucleotides in the transcript.

The nucleic acid sequences (b), (c-1), (c-2), where appropriate (c-3), and (d) under the control of the promoter (a) can preferably be transcribed to give a common transcript in which the nucleic acid sequences transcribed from the nucleic acid sequences (c-1) and/or (c-2) and/or, where appropriate, (c-3) and/or (d) are preferably active so as to increase the translation efficiency and/or the stability of the nucleic acid sequence transcribed from the transcribable nucleic acid sequence (b).

In particular embodiments, the nucleic acid sequence (d), when transcribed under the control of the promoter (a), codes for a nucleotide sequence of at least 40, preferably at least 80, preferably at least 100, and in particular about 120, consecutive A nucleotides in the transcript. The nucleic acid sequence (d), when transcribed under the control of the promoter (a), preferably codes for a nucleotide sequence of up to 500, preferably up to 400, preferably up to 300, preferably up to 200, and in particular up to 150, consecutive A nucleotides in the transcript.

In one embodiment, the nucleic acid molecule is characterized in that it can be cleaved, preferably enzymatically or in another biochemical way, within the nucleic acid sequence (d) in such a way that said cleavage results in a nucleic acid molecule which comprises, in the 5'→3' direction of transcription, the promoter (a), the nucleic acid sequence (b), the nucleic acid sequences (c-1), (c-2) and, where appropriate, (c-3), and at least a part of the nucleic acid sequence (d), wherein the at least a part of the nucleic acid sequence (d), when transcribed under the control of the promoter (a), codes for a nucleotide sequence of at least 20 consecutive A nucleotides in the transcript and wherein in the transcript the 3'-terminal nucleotide is an A nucleotide of said nucleotide sequence of at least 20 consecutive A nucleotides.

Preferably, after cleavage, said nucleic acid molecule, at the end of the strand that serves as template for the nucleotide sequence of at least 20 consecutive A nucleotides, has a T nucleotide which is part of the nucleotide sequence which serves as template for said nucleotide sequence of at least 20 consecutive A nucleotides in the transcript.

In particular embodiments, the at least part of the nucleic acid sequence (d), when transcribed under the control of the promoter (a), codes for a nucleotide sequence of at least 40, preferably at least 80, preferably at least 100, and in particular about 120, consecutive A nucleotides in the transcript. The nucleic acid sequence (d), when transcribed under the control of the promoter (a), preferably codes for a nucleotide sequence of up to 500, preferably up to 400, preferably up to 300, preferably up to 200, and in particular up to 150, consecutive A nucleotides in the transcript.

The nucleic acid molecule according to the invention is preferably a closed circular molecule prior to cleavage and a linear molecule after cleavage.

Preferably, cleavage is carried out with the aid of a restriction cleavage site which is preferably a restriction cleavage site for a type IIS restriction endonuclease.

In one embodiment, the recognition sequence for the type IIS restriction endonuclease is located 5-26 base pairs, preferably 24-26 base pairs, downstream of the 3' end of the nucleic acid sequence (d).

In preferred embodiments, the nucleic acid sequences (c-1), (c-2) and, where appropriate, (c-3) are independently of one another derived from a gene selected from the group consisting of globin genes such as alpha2-globin, alpha1-globin, beta-globin and growth hormone, preferably human beta-globin, and correspond, in a particularly preferred embodiment, to the nucleic acid sequence according to SEQ ID No. 1 of the sequence listing or to a nucleic acid sequence derived therefrom.

In a further aspect, the invention relates to a nucleic acid molecule comprising in the 5'→3' direction of transcription: (a) a promoter; (b) a transcribable nucleic acid sequence or a nucleic acid sequence for introducing a transcribable nucleic acid sequence; and (c) a nucleic acid sequence which, when transcribed under the control of the promoter (a), codes for a nucleotide sequence of at least 20 consecutive A nucleotides in the transcript.

The nucleic acid sequences (b) and (c) under the control of the promoter (a) can preferably be transcribed to give a common transcript in which the nucleic acid sequence transcribed from the nucleic acid sequence (c) is preferably active so as to increase the translation efficiency and/or the stability of the nucleic acid sequence transcribed from the transcribable nucleic acid sequence (b).

In particular embodiments, the nucleic acid sequence (c), when transcribed under the control of the promoter (a), codes for a nucleotide sequence of at least 40, preferably at least 80, preferably at least 100, and in particular about 120, consecutive A nucleotides in the transcript. The nucleic acid sequence (c), when transcribed under the control of the promoter (a), preferably codes for a nucleotide sequence of up to 500, preferably up to 400, preferably up to 300, preferably up to 200, and in particular up to 150, consecutive A nucleotides in the transcript.

In one embodiment, the nucleic acid molecule can be cleaved, preferably enzymatically or in another biochemical way, within the nucleic acid sequence (c) in such a way that said cleavage results in a nucleic acid molecule which comprises, in the 5'→3' direction of transcription, the promoter (a), the nucleic acid sequence (b), and at least a part of the nucleic acid sequence (c), wherein the at least a part of the nucleic acid sequence (c), when transcribed under the control of the promoter (a), codes for a nucleotide sequence of at least 20 consecutive A nucleotides in the transcript and wherein in the transcript the 3'-terminal nucleotide is an A nucleotide of said nucleotide sequence of at least 20 consecutive A nucleotides.

Preferably, after cleavage, the nucleic acid molecule, at the end of the strand that serves as template for the nucleotide sequence of at least 20 consecutive A nucleotides, has a T nucleotide which is part of the nucleotide sequence which serves as template for the nucleotide sequence of at least 20 consecutive A nucleotides in the transcript.

In particular embodiments, the at least a part of the nucleic acid sequence (c), when transcribed under the control of the promoter (a), codes for a nucleotide sequence of at least 40, preferably at least 80, preferably at least 100, and in particular about 120, consecutive A nucleotides in the transcript. The nucleic acid sequence (c), when transcribed under the control of the promoter (a), preferably codes for a nucleotide sequence of up to 500, preferably up to 400, preferably up to 300, preferably up to 200, and in particular up to 150, consecutive A nucleotides in the transcript.

The nucleic acid molecule is preferably a closed circular molecule prior to cleavage and a linear molecule after cleavage.

Preferably, cleavage is carried out with the aid of a restriction cleavage site which is preferably a restriction cleavage site for a type IIS restriction endonuclease.

In one embodiment, the recognition sequence for the type IIS restriction endonuclease is located 5-26 base pairs, preferably 24-26 base pairs, downstream of the 3' end of the nucleic acid sequence (c).

In one nucleic acid molecule according to the invention, the transcribable nucleic acid sequence preferably comprises a nucleic acid sequence coding for a peptide or protein and the nucleic acid sequence for introducing a transcribable nucleic acid sequence is preferably a multiple cloning site.

A nucleic acid molecule according to the invention may further comprise one or more members selected from the group consisting of: (i) a reporter gene; (ii) a selectable marker; and (iii) an origin of replication.

In one embodiment, a nucleic acid molecule according to the invention is in a closed circular conformation and preferably suitable for in vitro transcription of RNA, in particular mRNA, in particular after linearization.

In further aspects, the invention relates to a nucleic acid molecule obtainable by linearization of an above-described nucleic acid molecule, preferably by cleavage within the nucleic acid sequence which codes for a nucleotide sequence of at least 20 consecutive A nucleotides, and to RNA obtainable by transcription, preferably in vitro transcription, with above-described nucleic acid molecules under the control of the promoter (a).

In a further aspect, the invention relates to a method of transcribing in vitro a selected RNA molecule in order to increase its stability and/or translation efficiency, comprising: (i) coupling a first nucleic acid sequence (b-1) which corresponds to the 3'-untranslated region of a gene or is derived therefrom at the 3' end of a nucleic acid sequence (a) which can be transcribed to give said RNA molecule, (ii) coupling a second nucleic acid sequence (b-2) which corresponds to the 3'-untranslated region of a gene or is derived therefrom at the 3' end of said first nucleic acid sequence (b-1), and (iii) transcribing in vitro the nucleic acid obtained.

In a further aspect, the invention relates to a method of translating a selected mRNA molecule in order to increase expression thereof, comprising: (i) coupling a first nucleic acid sequence (b-1) which corresponds to the 3'-untranslated region of a gene or is derived therefrom at the 3' end of a nucleic acid sequence (a) which can be transcribed to give said mRNA molecule, (ii) coupling a second nucleic acid sequence (b-2) which corresponds to the 3'-untranslated region of a gene or is derived therefrom at the 3' end of said first nucleic acid sequence (b-1), and (iii) translating the mRNA which is obtainable by transcribing the nucleic acid obtained. Transcription is preferably carried out in vitro.

According to the invention, the term "coupling a nucleic acid sequence at the 3' end of a nucleic acid sequence" relates to a covalent linkage of the two nucleic acid sequences in such a way that the first nucleic acid sequence is downstream of the second nucleic acid sequence and may be separated from the latter by additional nucleic acid sequences.

In one embodiment, the methods according to the invention further comprise coupling at least one further nucleic acid sequence (b-3) which corresponds to the 3'-untranslated region of a gene or is derived therefrom at the 3' end of the second nucleic acid sequence (b-2).

The nucleic acid sequences (a), (b-1), (b-2) and, where appropriate, (b-3) can preferably be transcribed to give a common transcript in which the nucleic acid sequences transcribed from the nucleic acid sequences (b-1) and/or (b-2) and/or, where appropriate, (b-3) are preferably active so as to increase the translation efficiency and/or the stability of the nucleic acid sequence transcribed by the nucleic acid sequence (a).

In a further embodiment, the methods according to the invention further comprise coupling a nucleic acid sequence (c) which, when transcribed, codes for a nucleotide sequence of at least 20 consecutive A nucleotides, at the 3' end of the nucleic acid sequence (b-2) or, where appropriate, of the nucleic acid sequence (b-3).

The nucleic acid sequences (a), (b-1), (b-2) and, where appropriate, (b-3), and (c) can preferably be transcribed to give a common transcript in which the nucleic acid sequences transcribed from the nucleic acid sequences (b-1) and/or (b-2) and/or, where appropriate, (b-3), and/or (c) are preferably active so as to increase the translation efficiency and/or the stability of the nucleic acid sequence transcribed from the nucleic acid sequence (a).

In particular embodiments, the nucleic acid sequence (c), when transcribed, codes for a nucleotide sequence of at least 40, preferably at least 80, preferably at least 100, and in particular about 120, consecutive A nucleotides in the transcript. The nucleic acid sequence (c), when transcribed, preferably codes for a nucleotide sequence of up to 500, preferably up to 400, preferably up to 300, preferably up to 200, and in particular up to 150, consecutive A nucleotides in the transcript.

In particular embodiments, the methods according to the invention further comprise, prior to transcription of the nucleic acid obtained, cleavage within the nucleic acid sequence (c) in such a way that transcription of the nucleic acid obtained in this way generates a transcript which has the nucleic acid sequences transcribed from the nucleic acid sequences (a), (b-1), (b-2) and, where appropriate, (b-3) and a 3'-terminal nucleotide sequence of at least 20 consecutive A nucleotides, wherein the 3'-terminal nucleotide of said transcript is an A nucleotide of the nucleotide sequence of at least 20 consecutive A nucleotides.

In particular embodiments, the transcript has at its 3' end a nucleotide sequence of at least 40, preferably at least 80, preferably at least 100, and in particular about 120, consecutive A nucleotides. The transcript preferably has at its 3' end a nucleotide sequence of up to 500, preferably up to 400, preferably up to 300, preferably up to 200, and in particular up to 150, consecutive A nucleotides.

In preferred embodiments, the nucleic acid sequences (b-1), (b-2) and, where appropriate, (b-3) are independently of one another derived from a gene selected from the group consisting of globin genes such as alpha2-globin, alpha1-globin, beta-globin and growth hormone, preferably human beta-globin, and correspond, in a particularly preferred embodiment, to the nucleic acid sequence according to SEQ ID No. 1 of the sequence listing or to a nucleic acid sequence derived therefrom.

In a further aspect, the invention relates to a method of transcribing in vitro a selected RNA molecule in order to increase its stability and/or translation efficiency, comprising: (i) coupling a nucleic acid sequence (b) which, when transcribed, codes for a nucleotide sequence of at least 20 consecutive A nucleotides, at the 3' end of a nucleic acid sequence (a) which can be transcribed to give said RNA molecule, and (ii) transcribing in vitro the nucleic acid obtained.

In a further aspect, the invention relates to a method of translating a selected mRNA molecule in order to increase expression thereof, comprising: (i) coupling a nucleic acid sequence (b) which, when transcribed, codes for a nucleotide sequence of at least 20 consecutive A nucleotides, at the 3' end of a nucleic acid sequence (a) which can be transcribed to give said mRNA molecule, and (ii) translating the mRNA which is obtainable by transcribing the nucleic acid obtained. Transcription is preferably carried out in vitro.

The nucleic acid sequences (a) and (b) can preferably be transcribed to give a common transcript in which the nucleic acid sequence transcribed from the nucleic acid sequence (b) is preferably active so as to increase the translation efficiency and/or the stability of the nucleic acid sequence transcribed from the nucleic acid sequence (a).

In particular embodiments, the nucleic acid sequence (b), when transcribed, codes for a nucleotide sequence of at least 40, preferably at least 80, preferably at least 100, and in particular about 120, consecutive A nucleotides in the transcript. The nucleic acid sequence (b), when transcribed, preferably codes for a nucleotide sequence of up to 500, preferably up to 400, preferably up to 300, preferably up to 200, and in particular up to 150, consecutive A nucleotides in the transcript.

In particular embodiments, the methods according to the invention further comprise, prior to transcription of the nucleic acid obtained, cleavage within the nucleic acid sequence (b) in such a way that transcription of the nucleic acid obtained in this way generates a transcript which has the nucleic acid sequences transcribed from the nucleic acid sequence (a) and a 3'-terminal nucleotide sequence of at least 20 consecutive A nucleotides, wherein the 3'-terminal nucleotide of said transcript is an A nucleotide of the nucleotide sequence of at least 20 consecutive A nucleotides.

In particular embodiments, the transcript has at least 40, preferably at least 80, preferably at least 100, and in particular about 120, consecutive A nucleotides at its 3' end. The transcript preferably has up to 500, preferably up to 400, preferably up to 300, preferably up to 200, and in particular up to 150, consecutive A nucleotides at its 3' end.

In all aspects of the methods according to the invention, cleavage is preferably carried out with the aid of a restriction cleavage site which is preferably a restriction cleavage site for a type IIS restriction endonuclease.

In one embodiment, the recognition sequence for the type IIS restriction endonuclease is 5-26 base pairs, preferably 24-26 base pairs, downstream of the 3' end of the nucleic acid sequence which, when transcribed, codes for a nucleotide sequence of at least 20 consecutive A nucleotides.

The invention also relates to RNA obtainable by the methods according to the invention of transcribing in vitro a selected RNA molecule. The RNA preparation obtainable by the methods according to the invention of transcribing in vitro a selected RNA molecule from a nucleic acid molecule according to the invention as template is preferably homogeneous or essentially homogeneous with regard to the length of the poly(A) sequence of the RNA, i.e. the length of the poly(A) sequence in more than 90%, preferably more than 95%, preferably more than 98% or 99%, of the RNA molecules in the preparation differs by no more than 10, preferably no more than 5, 4, 3, 2 or 1, A nucleotides.

The invention may be utilized, for example, for increasing expression of recombinant proteins in cellular transcription and expression. More specifically, it is possible, when producing recombinant proteins, to introduce the modifications described according to the invention and a combination thereof into expression vectors and utilize them for the purpose of increasing transcription of recombinant nucleic acids and expression of recombinant proteins in cell-based systems. This includes, for example, the preparation of recombinant antibodies, hormones, cytokines, enzymes, and the like. This allows inter alia production costs to be reduced.

It is also possible to utilize the modifications described according to the invention and a combination thereof for gene therapy applications. Said modifications may be introduced into gene therapy vectors and thereby utilized for increasing expression of a transgen. To this end, any nucleic acid (DNA/RNA)-based vector systems (for example plasmids, adenoviruses, poxvirus vectors, influenza virus vectors, alphavirus vectors, and the like) may be used. Cells can be transfected with these vectors in vitro, for example in lymphocytes or dendritic cells, or else in vivo by direct administration.

It is further possible for the modifications described according to the invention and a combination thereof to increase the stability and/or expression efficiency of ribonucleic acids and thereby the amount of the peptides or proteins encoded by said ribonucleic acids. Coding ribonucleic acids may be employed, for example, for transient expression of genes, with possible fields of application being RNA-based vaccines which are transfected into cells in vitro or administered directly in vivo, transient expression of functional recombinant proteins in vitro, for example in order to initiate differentiation processes in cells or to study functions of proteins, and transient expression of functional recombinant proteins such as erythropoietin, hormones, coagulation inhibitors, etc., in vivo, in particular as pharmaceuticals.

RNA, in particular in vitro-transcribed RNA, modified by the modifications described according to the invention, may be used in particular for transfecting antigen-presenting cells and thus as a tool for delivering the antigen to be presented and for loading antigen-presenting cells, with said antigen to be presented corresponding to the peptide or protein expressed from said RNA or being derived therefrom, in particular by way of intracellular processing such as cleavage, i.e. the antigen to be presented is, for example, a fragment of the peptide or protein expressed from the RNA. Such antigen-presenting cells may be used for stimulating T cells, in particular CD4+ and/or CD8+ T cells.

The vectors allow RNA transcription under the control of an RNA polymerase 5' promoter and contain a polyadenyl cassette.

Figure 1A:
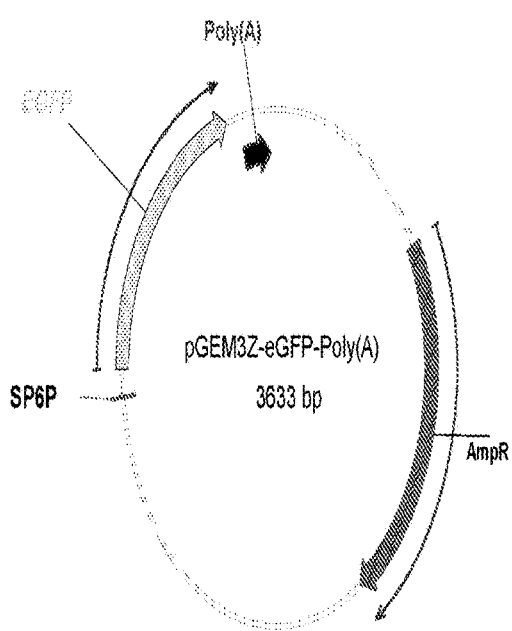
FIG. 1: Basic vectors used according to the invention for further cloning
Figure 1B:
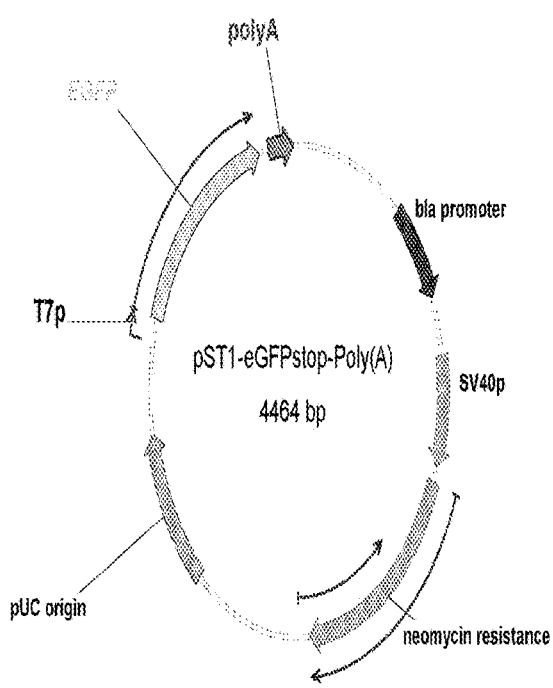
Figure 2:
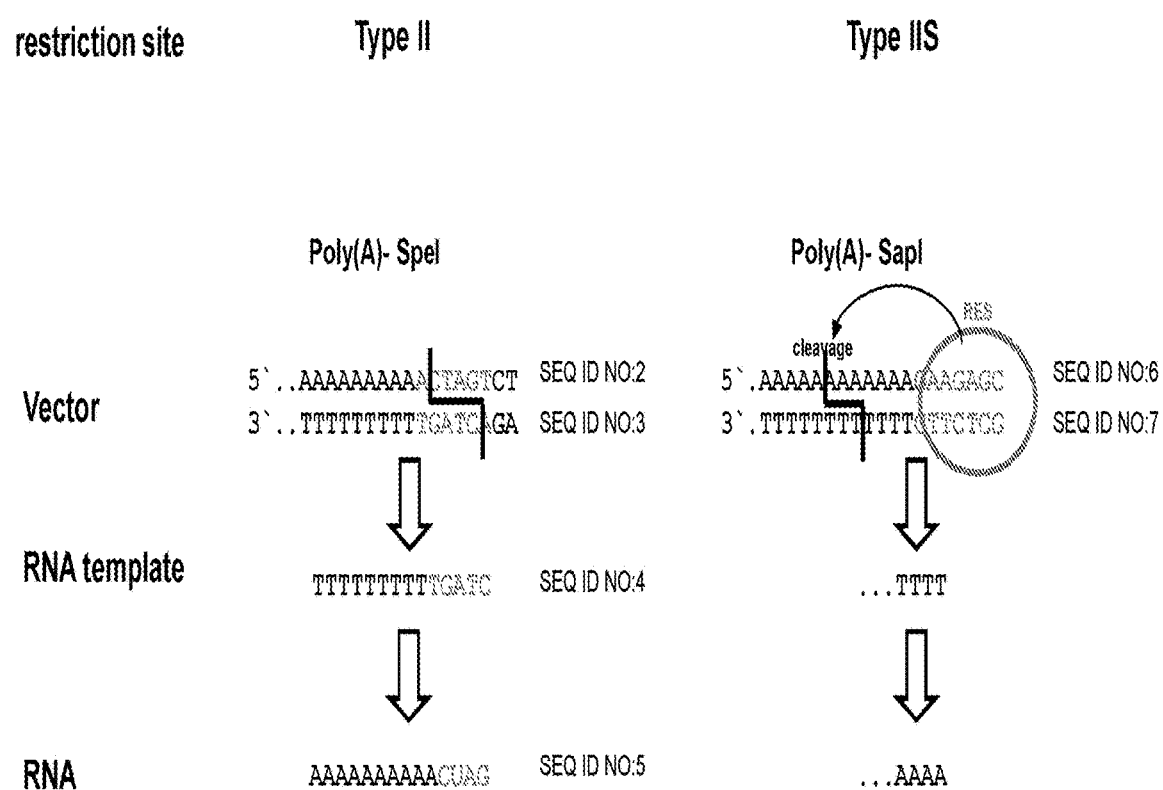
Figure 3A:
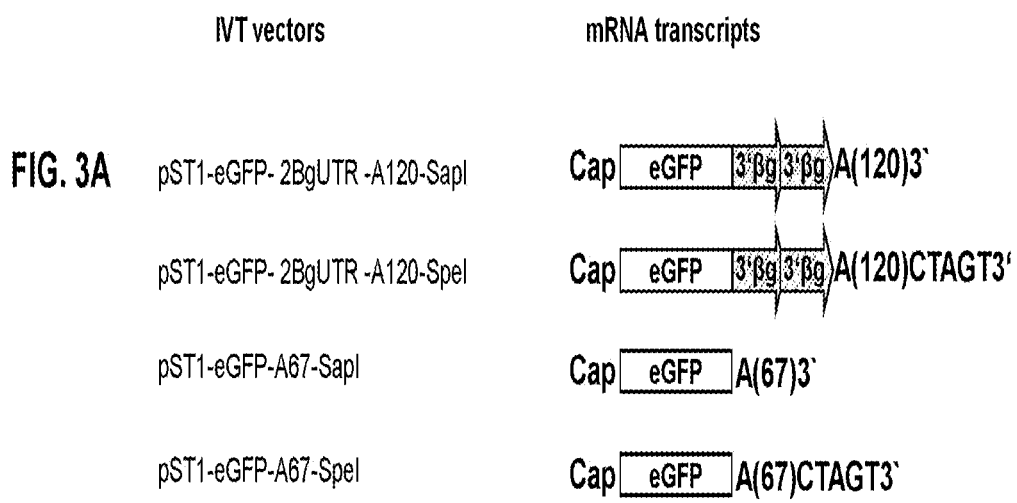
Figure 3B:
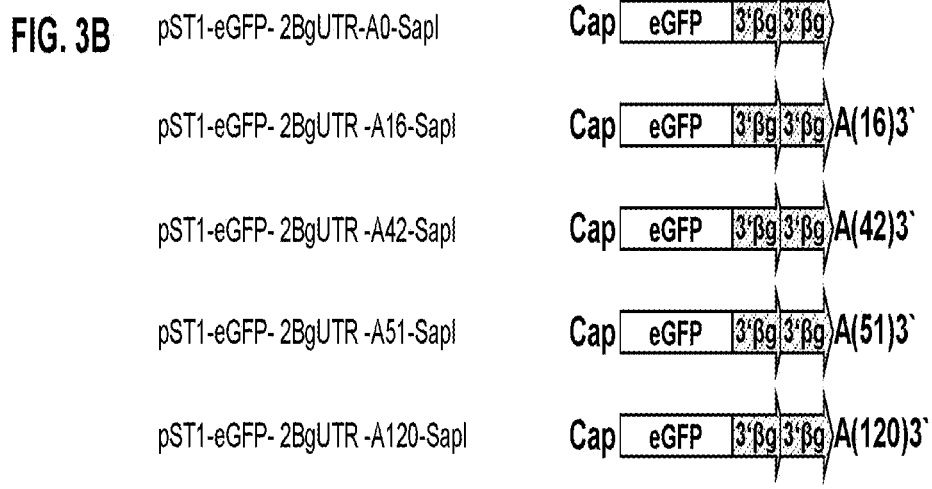
Figure 3C:
Figure 3C:
Figure 3C:
Figure 3D:
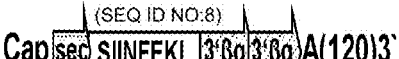
Figure 3D:
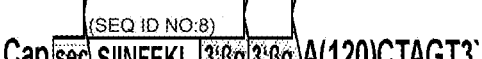
Figure 3D:
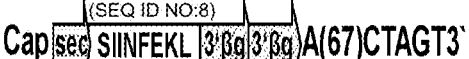
Figure 3D:
Figure 3D:
Figure 3D:
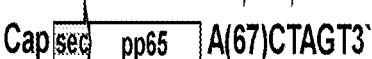

FIG. 2: Linearization of vectors (SEQ ID NOs:2-7) by type II restriction enzymes (e.g. SpeI) in comparison with type IIS restriction enzymes (e.g. SapI)

By introducing a type IIS restriction cleavage site whose recognition sequence is located 3' of the poly(A) sequence, while the cleavage site is 24-26 bp upstream and thus located within the poly(A) sequence, it is possible to linearize a plasmid within the poly(A) sequence.

FIG. 3: Vectors prepared according to the invention as template for in vitro transcription In order to study the effects of RNA modifications according to the invention on the level and duration of expression, a number of vectors were prepared which subsequently served as template for in vitro transcription. a. Vectors with masked versus unmasked poly(A) sequence; b. Vectors with poly(A) sequences of different length; c. Vectors with 3'-untranslated region of human beta-globin; d. SIINFEKL (SEQ ID NO: 8) and pp65 vectors; Cap—5'-capping; eGFP—GFP reporter gene; 3'βg—3'-untranslated region of β-globin; A(x)—x refers to the number of A nucleotides in the poly(A) sequence.

Figure 4:
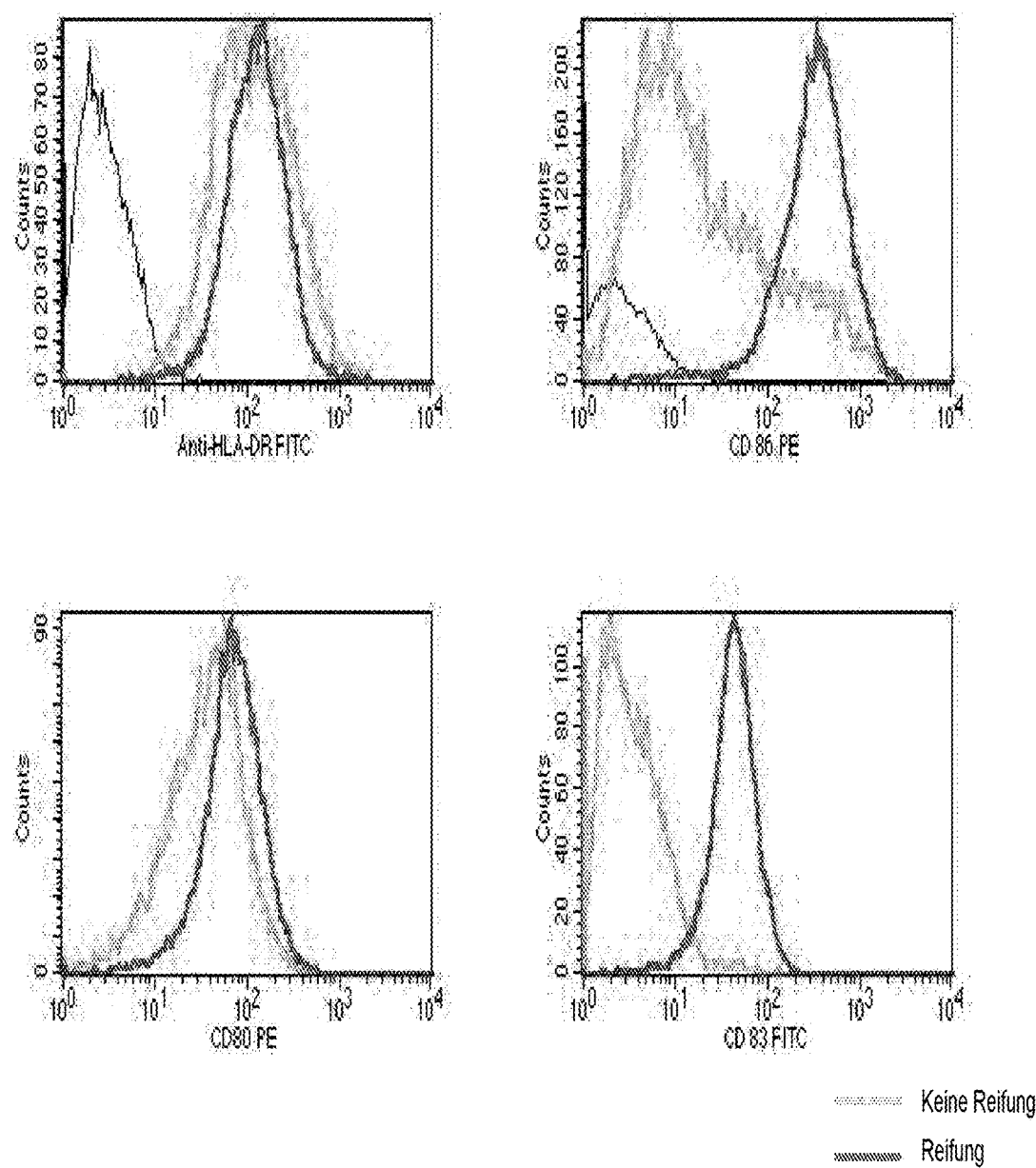

FIG. 4: Determination of the maturation state of immature versus mature dendritic cells by way of the surface markers indicated The effect of the RNA modifications according to the invention was tested in human dendritic cells (DCs), with an immunogenic stimulus triggering a DC maturation process. The DCs were stained with anti-CD80, anti-CD83, anti-CD86 and anti-HLA-DR antibodies which recognize specific DC maturation markers, and analyzed by flow cytometry.

FIG. 5: Influence of free versus masked poly(A) sequence on translation efficiency and transcript stability a. Influence of free versus masked poly(A) sequence on the translation efficiency of eGFP RNA in K562 cells and dendritic cells by way of determining the mean fluorescence intensity [MFI] in FACS-Kalibur; b. Influence of free versus masked poly(A) sequence on the transcript stability of eGFP RNA in immature dendritic cells after 48 h. In both the tumor cell line and in immature DCs, RNA with an open-ended poly(A) sequence is translated more efficiently and over a longer period than RNA with a masked-end poly(A) sequence. The translation efficiency for an unmasked-end poly(A) sequence in DCs is increased by a factor of 1.5, with poly(A) sequences of equal length. An open-ended poly(A) sequence moreover results in higher RNA stability.

FIG. 6: Influence of poly(A) sequence length on translation efficiency and transcript stability a. Influence of poly(A) sequence length on the translation efficiency of eGFP RNA in K562 cells and dendritic cells; b. Influence of poly(A) sequence length on the translation efficiency of d2eGFP RNA in K562 cells and dendritic cells; c. Influence of poly(A) sequence length on the transcript stability of eGFP RNA in K562 cells 48 h after electroporation. Extending the poly(A) sequence up to 120 A nucleotides increases the stability and translation of the transcript. An extension in excess of this has no positive effect. Extending the poly(A) sequence from 51 to 120 A nucleotides produces a 1.5 to 2-fold increase in translation efficiency. This effect is also reflected in RNA stability.

Figure 7:
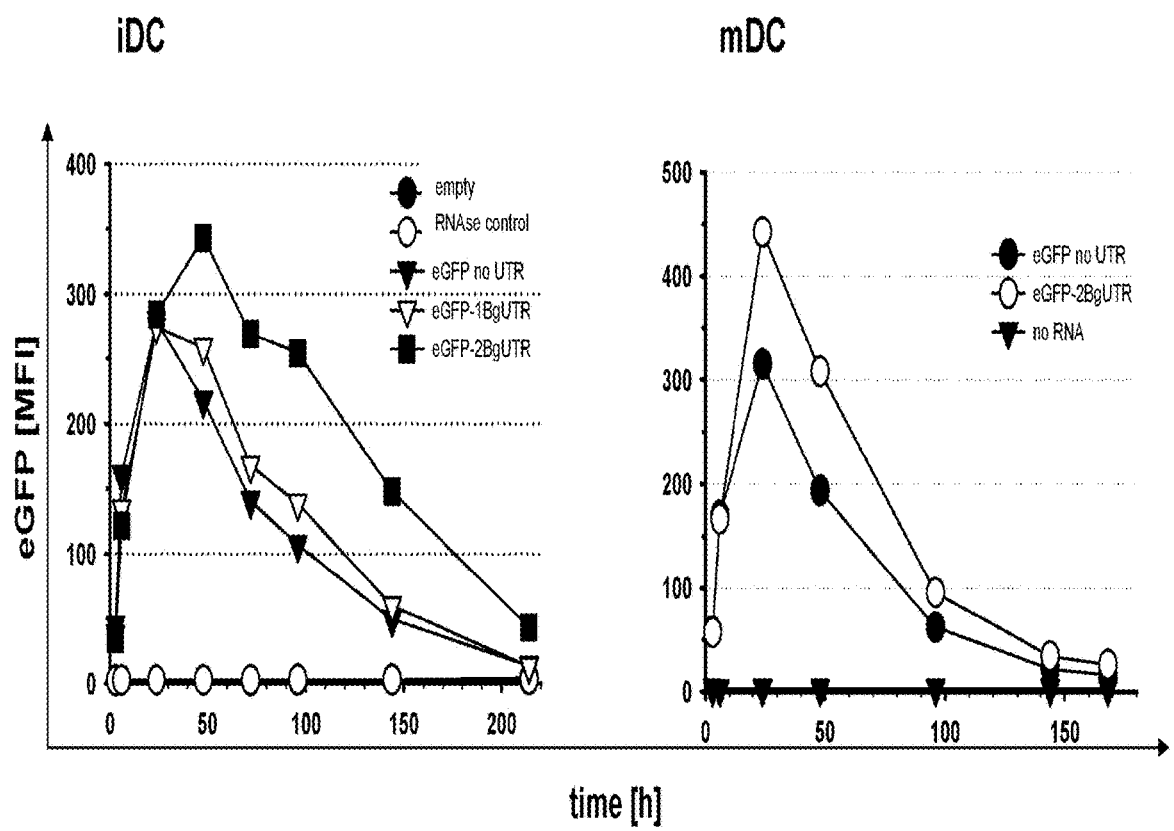

FIG. 7: Influence of a 3'-untranslated region of human beta-globin (BgUTR) on translation efficiency in immature and mature DCs Introducing a 3'-untranslated region of human beta-globin results in increasing expression of the RNA transcript. A double 3'-untranslated region of human beta-globin enhances the level of expression after 24 h, with said level markedly exceeding the combined effect of two individual 3'-untranslated regions of human beta-globin.

Figure 8:
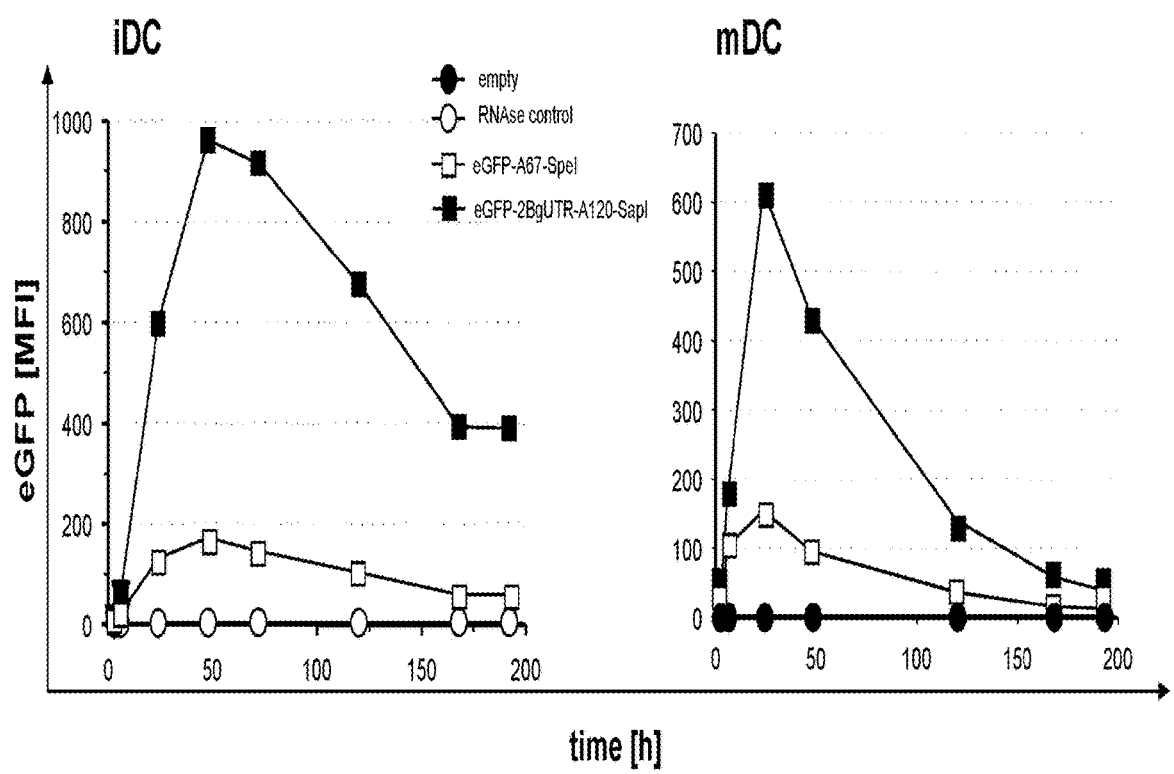

FIG. 8: Effect of the combined modifications according to the invention on translation efficiency in immature and mature DCs The translation efficiency of eGFP in immature and mature DCs can be increased by a factor of more than five by combining the RNA transcript modifications described according to the invention.

Figure 9:
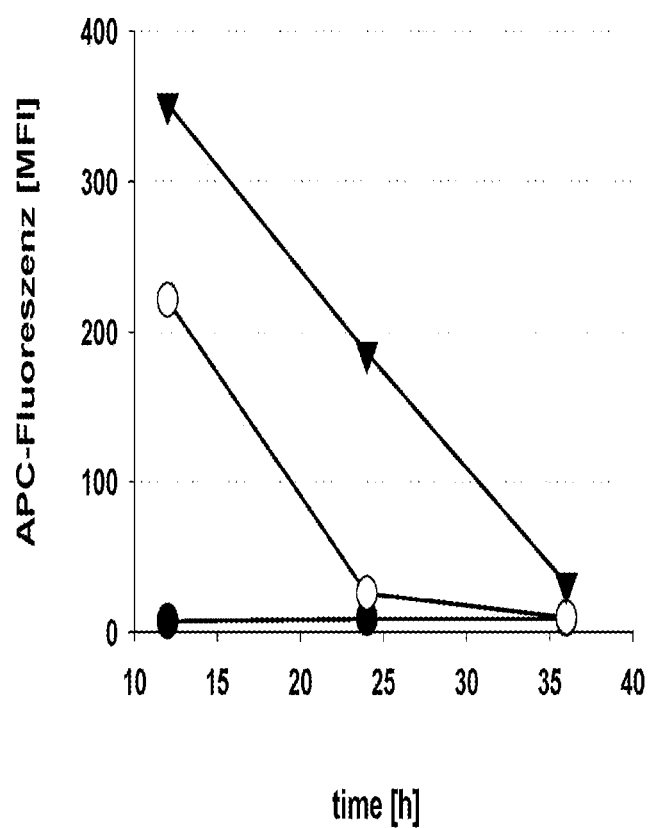

FIG. 9: Effect of the combined modifications according to the invention on the presentation of peptides by MHC molecules on EL4 cells Using the RNA constructs modified according to the invention results in enhanced presentation of peptide-MHC complexes on the cell surface, due to increased translation efficiency. In the IVT vectors described, eGFP was replaced with the OVA257-264 epitope (SIINFEKL) and EL4 cells (murine, T cell lymphoma) were used as target cells for transfection.

Figure 10:
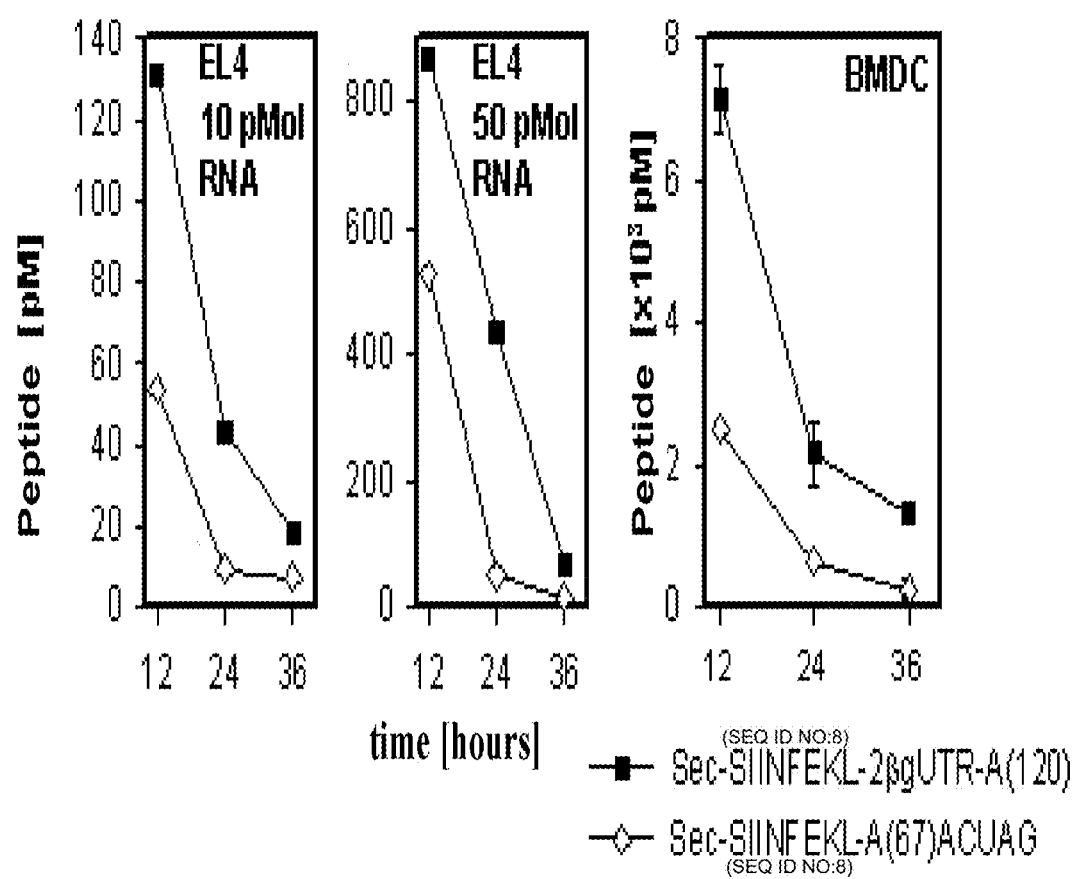

FIG. 10: Increase of antigen-specific peptide/MHC complexes by using IVT RNA constructs stabilized according to the invention Cells were electroporated with Sec-SIINFEKL (SEQ ID NO: 8)—A67-ACUAG RNA or Sec-SIINFEKL (SEQ ID NO: 8)—2BgUTR-A120 RNA (EL4 cells: 10 μmol, 50 pmol; C57B1/J6 immature BMDCs in triplicates: 150 μmol). Electroporation with buffer only was used as control. Cells were stained with 25D1.16 antibodies with regard to SIINFEKL/$K^b$ complexes. SIINFEKL peptide (SEQ ID NO: 8) concentrations were calculated from the average fluorescence values of living cells, using a peptide titration as standard curve. BMDC data are shown as averages of three experiments SEM.

FIG. 11: Effect of IVT RNA constructs stabilized according to the invention on T cell stimulation in vivo and in vitro (A) Improved in vivo T cell expansion by using stabilized IVT RNA constructs. $1\times10^5$ TCR-transgenic CD8+OT-I cells were adoptively transferred into C57B1/J6 mice. BMDCs of C57B1/J6 mice were transfected with 50 pmol of RNA (Sec-SIINFEKL(SEQ ID NO: 8)-A67-ACUAG, Sec-SIINFEKL(SEQ ID NO: 8)-2BgUTR-A120 or control RNA), matured with poly(I:C) (50 μg/ml) for 16 h and injected i.p. one day after T cell transfer (n=3). Peripheral blood was taken on day 4 and stained for SIINFEKL (SEQ ID NO: 8) tetramer-positive CD8$^+$ T cells. Dot blots depict CD8$^+$ T cells, and the numbers indicated represent the percentage of tetramer-positive CD8$^+$ T cells.

(B) Improved in vitro expansion of human T cells containing stabilized IVT RNA constructs. CD8$^+$ and CD4$^+$ lymphocytes from HCMV-seropositive healthy donors were cocultured with autologous DCs which had been transfected with Sec-pp65-A67-ACUAG RNA, Sec-pp65-2BgUTR-A120 RNA, or control RNA (data not shown) or pulsed with pp65 peptide pool (1.75 μg/ml) as positive control. After expansion for 7 days, each effector cell population ($4\times10^4$/well) was assayed in an IFN-γ-ELISpot with autologous DCs ($3\times10^4$/well) which had been loaded either with pp65 peptide pool or an irrelevant peptide pool (1.75 μg/ml). The graphic representation depicts the average number of spots of triplicate measurements±SEM.

DETAILED DESCRIPTION OF PREFERRED EMBODIMENTS

According to the invention, standard methods may be used for preparing recombinant nucleic acids, culturing cells and introducing nucleic acids, in particular RNA, into cells, in particular electroporation and lipofection. Enzymatic reactions are carried out according to the manufacturers' instructions or in a manner known per se.

According to the invention, a nucleic acid molecule or a nucleic acid sequence refers to a nucleic acid which is preferably deoxyribonucleic acid (DNA) or ribonucleic acid (RNA). According to the invention, nucleic acids comprise genomic DNA, cDNA, mRNA, recombinantly prepared and chemically synthesized molecules. According to the invention, a nucleic acid may be in the form of a single-stranded or double-stranded and linear or covalently closed circular molecule.

"mRNA" means "messenger RNA" and refers to a "transcript" which is produced using DNA as template and which itself codes for a peptide or protein. An mRNA typically comprises a 5'-untranslated region, a protein-encoding region and a 3'-untranslated region. mRNA has a limited half time both in cells and in vitro. According to the invention, mRNA may be prepared from a DNA template by in vitro transcription. It may be modified by further stabilizing modifications and capping, in addition to the modifications according to the invention.

The term "nucleic acid" furthermore also comprises a chemical derivatization of a nucleic acid on a nucleotide base, on the sugar or on the phosphate, and nucleic acids containing non-natural nucleotides and nucleotide analogs.

According to the invention, a "nucleic acid sequence which is derived from a nucleic acid sequence" refers to a nucleic acid containing, in comparison with the nucleic acid from which it is derived, single or multiple nucleotide substitutions, deletions and/or additions and which is preferably complementary to the nucleic acid from which it is derived, i.e. there is a certain degree of homology between said nucleic acids and the nucleotide sequences of said nucleic acids correspond in a significant direct or complementary manner. According to the invention, a nucleic acid derived from a nucleic acid has a functional property of the nucleic acid from which it is derived. Such functional properties include in particular the ability to increase, in a functional linkage to a nucleic acid which can be transcribed into RNA (transcribable nucleic acid sequence), the stability and/or translation efficiency of RNA produced from this nucleic acid in the complete RNA molecule.

According to the invention, "functional linkage" or "functionally linked" relates to a connection within a functional relationship. A nucleic acid is "functionally linked" if it is functionally related to another nucleic acid sequence. For example, a promoter is functionally linked to a coding sequence if it influences transcription of said coding sequence. Functionally linked nucleic acids are typically adjacent to one another, where appropriate separated by further nucleic acid sequences, and, in particular embodiments, are transcribed by RNA polymerase to give a single RNA molecule (common transcript).

The nucleic acids described according to the invention are preferably isolated. The term "isolated nucleic acid" means according to the invention that the nucleic acid has been (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid available to manipulation by recombinant DNA techniques.

A nucleic acid is "complementary" to another nucleic acid if the two sequences can hybridize with one another and form a stable duplex, said hybridization being carried out preferably under conditions which allow specific hybridization between polynucleotides (stringent conditions). Stringent conditions are described, for example, in Molecular Cloning: A Laboratory Manual, J. Sambrook et al., eds., 2nd edition, Cold Spring Harbor Laboratory Press, Cold Spring Harbor, New York 1989 or Current Protocols in Molecular Biology, F. M. Ausubel et al., eds., John Wiley & Sons, Inc., New York, and refer, for example, to a hybridization at 65° C. in hybridization buffer (3.5×SSC, 0.02% Ficoll, 0.02% polyvinylpyrrolidone, 0.02% bovine serum albumin, 2.5 mM $NaH_2PO_4$ (pH7), 0.5% SDS, 2 mM EDTA). SSC is 0.15 M sodium chloride/0.15 M sodium citrate, pH 7. After hybridization, the membrane to which the DNA has been transferred, is washed, for example, in 2×SSC at room temperature and then in 0.1-0.5×SSC/0.1×SDS at temperatures up to 68° C.

According to the invention, complementary nucleic acids have nucleotides which are at least 60%, at least 70%, at least 80%, at least 90%, and preferably at least 95%, at least 98% or at least 99%, identical.

The term "% identical" is intended to refer to a percentage of nucleotides which are identical in an optimal alignment between two sequences to be compared, with said percentage being purely statistical, and the differences between the two sequences may be randomly distributed over the entire length of the sequence and the sequence to be compared may comprise additions or deletions in comparison with the reference sequence, in order to obtain optimal alignment between two sequences. Comparisons of two sequences are usually carried out by comparing said sequences, after optimal alignment, with respect to a segment or "window of comparison", in order to identify local regions of corresponding sequences. The optimal alignment for a comparison may be carried out manually or with the aid of the local homology algorithm by Smith and Waterman, 1981, Ads App. Math. 2, 482, with the aid of the local homology algorithm by Neddleman and Wunsch, 1970, J. Mol. Biol. 48, 443, and with the aid of the similarity search algorithm by Pearson and Lipman, 1988, Proc. Natl Acad. Sci. USA 85, 2444 or with the aid of computer programs using said algorithms (GAP, BESTFIT, FASTA, BLAST P, BLAST N and TFASTA in Wisconsin Genetics Software Package, Genetics Computer Group, 575 Science Drive, Madison, Wis.).

Percentage identity is obtained by determining the number of identical positions in which the sequences to be compared correspond, dividing this number by the number of positions compared and multiplying this result by 100.

For example, the BLAST program "BLAST 2 sequences" may be used.

"3' end of a nucleic acid" refers according to the invention to that end which has a free hydroxy group. In a diagrammatic representation of double-stranded nucleic acids, in particular DNA, the 3' end is always on the right-hand side. "5' end of a nucleic acid" refers according to the invention to that end which has a free phosphate group. In a diagrammatic representation of double-strand nucleic acids, in particular DNA, the 5' end is always on the left-hand side.

5' end 5'-P—NNNNNNN—OH-3' 3' end
3'-HO—NNNNNNN—P-5'

In particular embodiments, a nucleic acid is functionally linked according to the invention to expression control sequences which may be homologous or heterologous with respect to the nucleic acid.

A transcribable nucleic acid, in particular a nucleic acid coding for a peptide or protein, and an expression control sequence are "functionally" linked to one another, if they are covalently linked to one another in such a way that transcription or expression of the transcribable and in particular coding nucleic acid is under the control or under the influence of the expression control sequence. If the nucleic acid is to be translated into a functional peptide or protein, induction of an expression control sequence functionally linked to the coding sequence results in transcription of said coding sequence, without causing a frame shift in the coding sequence or the coding sequence being unable to be translated into the desired peptide or protein.

The term "expression control sequence" comprises according to the invention promoters, ribosome-binding sequences and other control elements which control transcription of a gene or translation of the derived RNA. In particular embodiments of the invention, the expression control sequences can be regulated. The precise structure of expression control sequences may vary depending on the species or cell type but usually includes 5'-untranscribed and 5'- and 3'-untranslated sequences involved in initiating transcription and translation, respectively, such as TATA box, capping sequence, CAAT sequence and the like. More specifically, 5'-untranscribed expression control sequences include a promoter region which encompasses a promoter sequence for transcription control of the functionally linked gene. Expression control sequences may also include enhancer sequences or upstream activator sequences.

The nucleic acids specified herein, in particular transcribable and coding nucleic acids, may be combined with any expression control sequences, in particular promoters, which may be homologous or heterologous to said nucleic acids, with the term "homologous" referring to the fact that a nucleic acid is also functionally linked naturally to the expression control sequence, and the term "heterologous" referring to the fact that a nucleic acid is not naturally functionally linked to the expression control sequence.

The term "promoter" or "promoter region" refers to a DNA sequence upstream (5') of the coding sequence of a gene, which controls expression of said coding sequence by providing a recognition and binding site for RNA polymerase. The promoter region may include further recognition or binding sites for further factors involved in regulating transcription of said gene. A promoter may control transcription of a prokaryotic or eukaryotic gene. A promoter may be "inducible" and initiate transcription in response to an inducer, or may be "constitutive" if transcription is not controlled by an inducer. An inducible promoter is expressed only to a very small extent or not at all, if an inducer is absent. In the presence of the inducer, the gene is "switched on" or the level of transcription is increased. This is usually mediated by binding of a specific transcription factor.

Examples of promoters preferred according to the invention are promoters for SP6, T3 or T7 polymerase.

According to the invention, the term "expression" is used in its most general meaning and comprises production of RNA or of RNA and protein. It also comprises partial expression of nucleic acids. Furthermore, expression may be transient or stable. With respect to RNA, the term "expression" or "translation" refers in particular to production of peptides or proteins.

The term "nucleic acids which can be transcribed to give a common transcript" means that said nucleic acids are functionally linked to one another in such a way that, where appropriate after linearization such as restriction enzyme cleavage of the nucleic acid molecule comprising said nucleic acids, in particular of a closed circular nucleic acid molecule, transcription under the control of a promoter results in an RNA molecule comprising the transcripts of said nucleic acids covalently bound to one another, where appropriate separated by sequences located inbetween.

According to the invention, the term "transcription" comprises "in vitro transcription", wherein the term "in vitro transcription" relates to a method in which RNA, in particular mRNA, is synthesized in vitro in a cell-free manner, i.e. preferably by using appropriately prepared cell extracts. The preparation of transcripts preferably makes use of cloning vectors which are generally referred to as transcription vectors and which are included according to the invention under the term "vector".

The term "nucleic acid sequence transcribed from a nucleic acid sequence" refers to RNA, where appropriate as part of a complete RNA molecule, which is a transcription product of the latter nucleic acid sequence.

The term "nucleic acid sequence which is active in order to increase the translation efficiency and/or stability of a nucleic acid sequence" means that the first nucleic acid is capable of modifying, in a common transcript with the second nucleic acid, the translation efficiency and/or stability of said second nucleic acid in such a way that said translation efficiency and/or stability is increased in comparison with the translation efficiency and/or stability of said second nucleic acid without said first nucleic acid. In this context, the term "translation efficiency" relates to the amount of translation product provided by an RNA molecule within a particular period of time and the term "stability" relates to the half life of an RNA molecule.

The 3'-untranslated region relates to a region which is located at the 3' end of a gene, downstream of the termination codon of a protein-encoding region, and which is transcribed but is not translated into an amino acid sequence.

According to the invention, a first polynucleotide region is considered to be located downstream of a second polynucleotide region, if the 5' end of said first polynucleotide region is the part of said first polynucleotide region closest to the 3' end of said second polynucleotide region.

The 3'-untranslated region typically extends from the termination codon for a translation product to the poly(A) sequence which is usually attached after the transcription process. The 3'-untranslated regions of mammalian mRNA typically have a homology region known as the AAUAAA hexanucleotide sequence. This sequence is presumably the poly(A) attachment signal and is frequently located from 10 to 30 bases upstream of the poly(A) attachment site.

3'-untranslated regions may contain one or more inverted repeats which can fold to give stem-loop structures which act as barriers for exoribonucleases or interact with proteins known to increase RNA stability (e.g. RNA-binding proteins).

5'- and/or 3'-untranslated regions may, according to the invention, be functionally linked to a transcribable and in particular coding nucleic acid, so as for these regions to be associated with the nucleic acid in such a way that the stability and/or translation efficiency of the RNA transcribed from said transcribable nucleic acid are increased.

The 3'-untranslated regions of immunoglobulin mRNAs are relatively short (fewer than about 300 nucleotides), while the 3'-untranslated regions of other genes are relatively long. For example, the 3'-untranslated region of tPA is about 800 nucleotides in length, that of factor VIII is about 1800 nucleotides in length and that of erythropoietin is about 560 nucleotides in length.

It can be determined according to the invention, whether a 3'-untranslated region or a nucleic acid sequence derived therefrom increases the stability and/or translation efficiency of RNA, by incorporating the 3'-untranslated region or the nucleic acid sequence derived therefrom into the 3'-untranslated region of a gene and measuring whether said incorporation increases the amount of protein synthesized.

The above applies accordingly to the case in which according to the invention a nucleic acid comprises two or more 3'-untranslated regions which are preferably coupled sequentially with or without a linker inbetween, preferably in a "head-to-tail relationship" (i.e. the 3'-untranslated regions have the same orientation, preferably the orientation naturally occurring in a nucleic acid).

According to the invention, the term "gene" refers to a particular nucleic acid sequence which is responsible for producing one or more cellular products and/or for achieving one or more intercellular or intracellular functions. More specifically, said term relates to a DNA section which comprises a nucleic acid coding for a specific protein or a functional or structural RNA molecule.

The terms "polyadenyl cassette" or "poly(A) sequence" refer to a sequence of adenyl residues which is typically located at the 3' end of an RNA molecule. The invention provides for such a sequence to be attached during RNA transcription by way of a DNA template on the basis of repeated thymidyl residues in the strand complementary to the coding strand, whereas said sequence is normally not encoded in the DNA but is attached to the free 3' end of the RNA by a template-independent RNA polymerase after transcription in the nucleus. According to the invention, a poly(A) sequence of this kind is understood as meaning a nucleotide sequence of at least 20, preferably at least 40, preferably at least 80, preferably at least 100 and preferably up to 500, preferably up to 400, preferably up to 300, preferably up to 200, and in particular up to 150, consecutive A nucleotides, and in particular about 120 consecutive A nucleotides, wherein the term "A nucleotides" refers to adenyl residues.

In a preferred embodiment, a nucleic acid molecule according to the invention is a vector. The term "vector" is used here in its most general meaning and comprises any intermediate vehicles for a nucleic acid which, for example, enable said nucleic acid to be introduced into prokaryotic and/or eukaryotic host cells and, where appropriate, to be integrated into a genome. Such vectors are preferably replicated and/or expressed in the cell. Vectors comprise plasmids, phagemids or virus genomes. The term "plasmid", as used herein, generally relates to a construct of extrachromosomal genetic material, usually a circular DNA duplex, which can replicate independently of chromosomal DNA.

According to the invention, the term "host cell" refers to any cell which can be transformed or transfected with an exogenous nucleic acid. The term "host cell" comprises, according to the invention, prokaryotic (e.g. *E. coli*) or eukaryotic cells (e.g. yeast cells and insect cells). Particular preference is given to mammalian cells such as cells from humans, mice, hamsters, pigs, goats, primates. The cells may be derived from a multiplicity of tissue types and comprise primary cells and cell lines. Specific examples include keratinocytes, peripheral blood leukocytes, bone marrow stem cells and embryonic stem cells. In other embodiments, the host cell is an antigen-presenting cell, in particular a dendritic cell, a monocyte or a macrophage. A nucleic acid may be present in the host cell in a single or in several copies and, in one embodiment is expressed in the host cell.

According to the invention, a peptide or protein encoded by a nucleic acid may be a peptide or protein which is located in the cytoplasma, in the nucleus, in the membrane, in organelles or is secreted. They include structural proteins, regulatory proteins, hormones, neurotransmitters, growth-regulating factors, differentiation factors, gene expression-regulating factors, DNA-associated proteins, enzymes, serum proteins, receptors, medicaments, immunomodulators, oncogenes, toxins, tumor antigens or antigens. Said peptides or proteins may have a naturally occurring sequence or a mutated sequence in order to enhance, inhibit, regulate or eliminate their biological activity.

The term "peptide" refers to substances which comprise two or more, preferably 3 or more, preferably 4 or more, preferably 6 or more, preferably 8 or more, preferably 10 or more, preferably 13 or more, preferably 16 or more, preferably 20 or more, and up to preferably 50, preferably 100 or preferably 150, consecutive amino acids linked to one another via peptide bonds. The term "protein" refers to large peptides, preferably peptides having at least 151 amino acids, but the terms "peptide" and "protein" are used herein usually as synonyms. The terms "peptide" and "protein" comprise according to the invention substances which contain not only amino acid components but also non-amino acid components such as sugars and phosphate structures, and also comprise substances containing bonds such as ester, thioether or disulfide bonds.

The invention provides for nucleic acids, in particular RNA, to be administered to a patient. In one embodiment, nucleic acids are administered by ex vivo methods, i.e. by removing cells from a patient, genetically modifying said cells and reintroducing the modified cells into the patient. Transfection and transduction methods are known to the skilled worker. The invention also provides for nucleic acids to be administered in vivo.

According to the invention, the term "transfection" refers to introducing one or more nucleic acids into an organism or into a host cell. Various methods may be employed in order to introduce according to the invention nucleic acids into cells in vitro or in vivo. Such methods include transfection of nucleic acid-CaPO$_4$ precipitates, transfection of nucleic acids associated with DEAE, transfection or infection with viruses carrying the nucleic acids of interest, liposome-mediated transfection, and the like. In particular embodiments, preference is given to directing the nucleic acid to particular cells. In such embodiments, a carrier used for administering a nucleic acid to a cell (e.g. a retrovirus or a liposome) may have a bound targeting molecule. For example, a molecule such as an antibody specific to a surface membrane protein on the targeted cell, or a ligand for a receptor on the target cell may be incorporated into or bound to the nucleic acid carrier. If administration of a nucleic acid by liposomes is desired, proteins binding to a surface membrane protein associated with endocytosis may be incorporated into the liposome formulation in order to enable targeting and/or absorption. Such proteins include capsid proteins or fragments thereof which are specific to a particular cell type, antibodies to proteins that are internalized, proteins targeting an intracellular site, and the like.

"Reporter" relates to a molecule, typically a peptide or protein, which is encoded by a reporter gene and measured in a reporter assay. Conventional systems usually employ an enzymatic reporter and measure the activity of said reporter.

The term "multiple cloning site" refers to a nucleic acid region containing restriction enzyme sites, any one of which may be used for cleavage of, for example, a vector and insertion of a nucleic acid.

According to the invention, two elements such as nucleotides or amino acids are consecutive, if they are directly adjacent to one another, without any interruption. For example, a sequence of x consecutive nucleotides N refers to the sequence $(N)_x$.

"Restriction endonuclease" or "restriction enzyme" refers to a class of enzymes that cleave phosphodiester bonds in both strands of a DNA molecule within specific base sequences. They recognize specific binding sites, referred to as recognition sequences, on a double-stranded DNA molecule. The sites at which said phosphodiester bonds in the DNA are cleaved by said enzymes are referred to as cleavage sites. In the case of type IIS enzymes, the cleavage site is located at a defined distance from the DNA binding site. According to the invention, the term "restriction endonuclease" comprises, for example, the enzymes SapI, EciI, BpiI, AarI, AloI, BaeI, BbvCI, PpiI and PsrI, BsrDI, BtsI, EarI, BmrI, BsaI, BsmBI, FauI, BbsI, BciVI, BfuAI, BspMI, BseRI, EciI, BtgZI, BpuEI, BsgI, MmeI, CspCI, BaeI, BsaMI, Mva1269I, PctI, Bse3DI, BseMI, Bst6I, Eam1104I, Ksp632I, BfiI, Bso31I, BspTNI, Eco31I, Esp3I, BfuI, Acc36I, AarI, Eco57I, Eco57MI, GsuI, AloI, Hin4I, PpiI, and PsrI.

"Half life" refers to the time required for eliminating half of the activity, amount or number of molecules.

The present invention is described in detail by the following figures and examples which should be construed by way of illustration only and not by way of limitation. On the basis of the description and the examples, further embodiments are accessible to the skilled worker and are likewise within the scope of the invention.

EXAMPLES

Example 1: Preparation of Vectors and In Vitro Transcription of RNA

In order to study the effects of the RNA modifications according to the invention on the level and duration of expression, a number of IVT vectors were prepared which served as template for in vitro transcription (FIG. 3).

The reporter genes for eGFP and d2eGFP, two molecules with different half lives (HL), were inserted into the vectors, thereby enabling the influence of the RNA modifications according to the invention to be analyzed. Fluorescence decreases with an average HL of 17.3 h for eGFP and 2 h for d2eGFP. These constructs were used for preparing in vitro-transcribed eGFP RNA and d2eGFP RNA, respectively.

Example 2: Transfection of Cells with the In Vitro-Transcribed RNA Modified According to the Invention and Effect on RNA Translation and Stability In vitro-transcribed eGFP RNA and d2eGFP RNA were used for transfecting K562 cells (human, leukemia) by means of electroporation. The transfection efficiency was >90% in K562 cells.

This was followed by assaying the action of the RNA modifications described in human dendritic cells (DCs) which are the most important modulators of the immune system. This approach is immunologically relevant because RNA-transfected DCs can be considered for vaccination. Immature DCs are located in the skin and in peripheral organs. Here they are in an immature state which is characterized by well-studied surface markers and which is functionally distinguished by high endocytotic activity. An immunogenic stimulus such as, for example, an infection with pathogens, triggers a DC maturation process. At the same time, said stimulus initiates DC migration into the regional lymph nodes, where said DCs are the most effective inducers of T cell and B cell immune responses. The mature state of said DCs is also characterized by expression of surface markers and cytokines studied in detail and by a characteristic DC morphology. There are established cell culture systems for differentiating immature human DCs from blood monocytes. These may be caused to mature by various stimuli.

The transfection efficiency in primary dendritic cells was 70-80%. The DCs were stained with anti-CD80, anti-CD83, anti-CD86 and anti-HLA-DR antibodies which recognize specific DC maturation markers, and analyzed by flow cytometry (FIG. 4).

The level and duration of expression were determined with the aid of FACS-Kalibur by way of determining the eGFP fluorescence intensity. The amount of RNA in the cells was determined with the aid of a quantitative RT-PCR.

a. Effect of an Open-Ended Poly(A) Sequence on RNA Translation and Stability

Figure 5B:
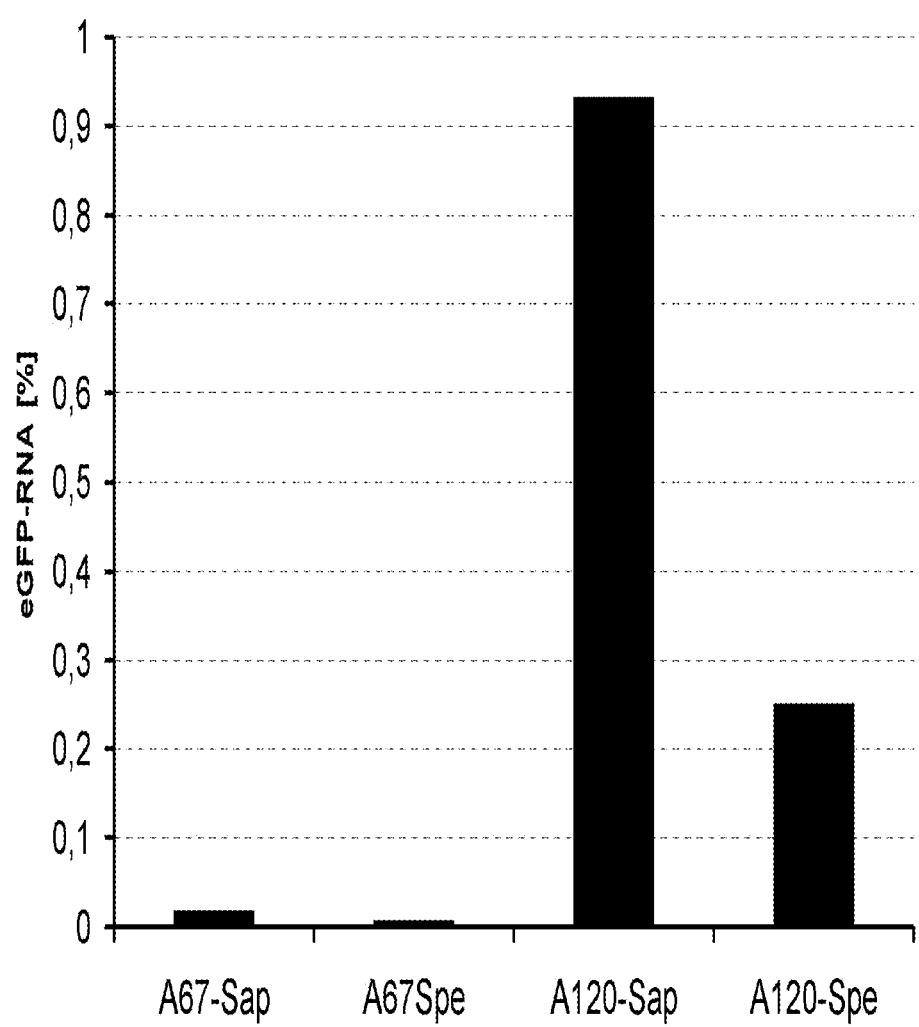

Both the tumor cell line K562 and immature DCs (iDC) were shown to translate RNA having an open-ended poly(A) sequence more efficiently and over a longer period of time than RNA having a masked-end poly(A) sequence (FIG. 5a). The translation efficiency for an unmasked-end poly(A) sequence in immature DCs is increased by a factor of 1.5, with poly(A) sequences of equal length. Moreover, said modification results in higher RNA stability (FIG. 5b). A 4 to 5-fold amount of RNA can be detected in immature DCs which had been transfected with RNA having an unmasked poly(A) sequence 48 h after electroporation.

b. Effect of the Poly(A) Sequence Length on RNA Translation and Stability

Figure 6A:
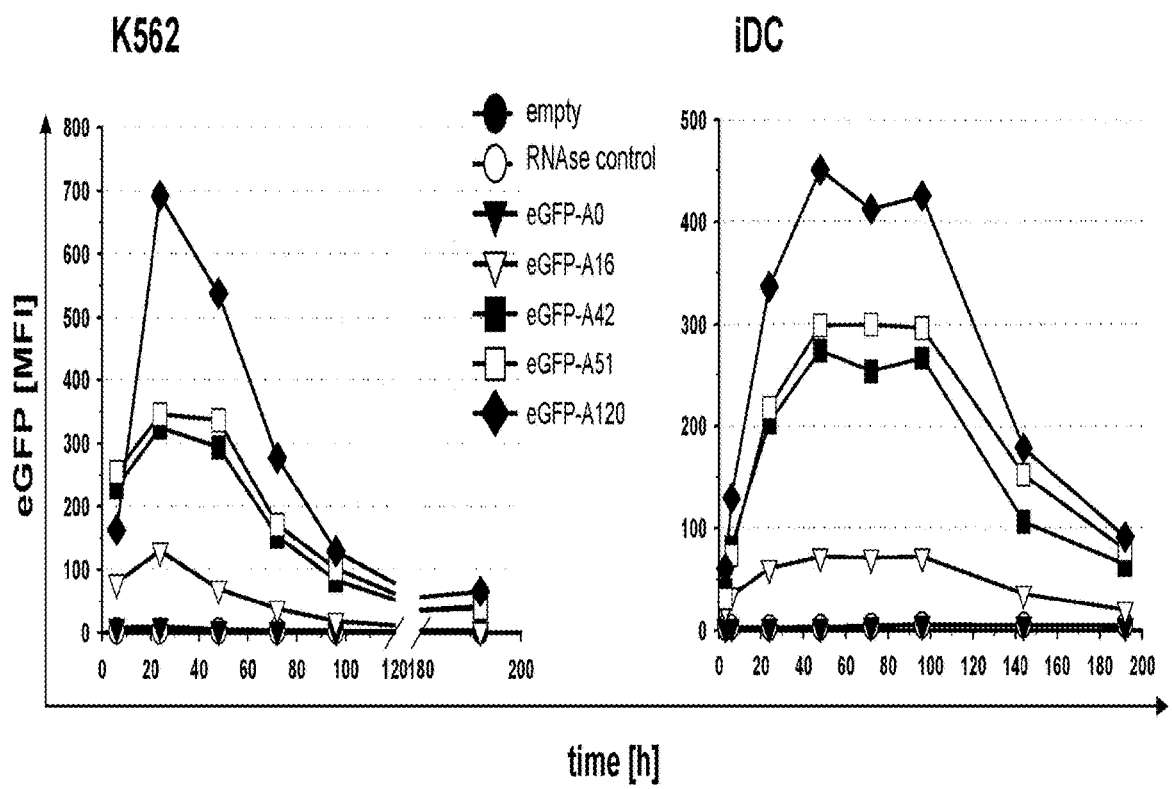
Figure 6B:
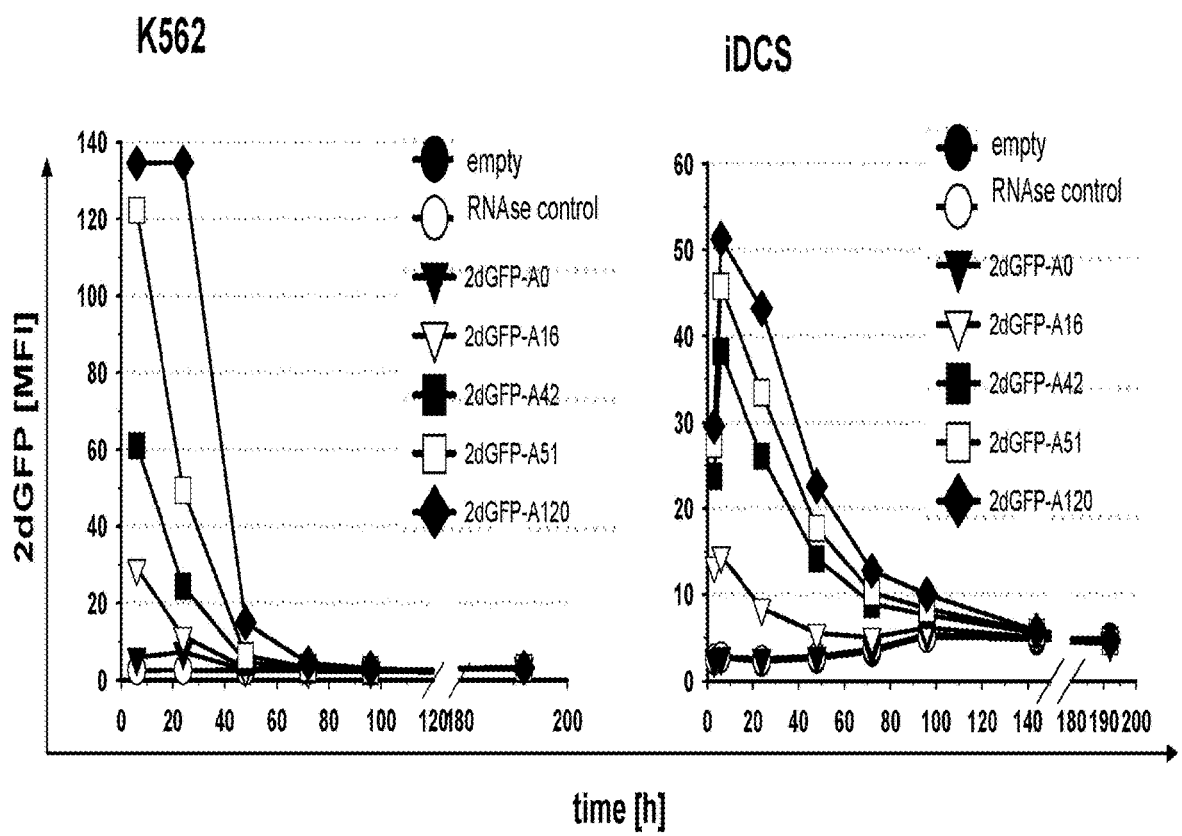
Figure 6C:
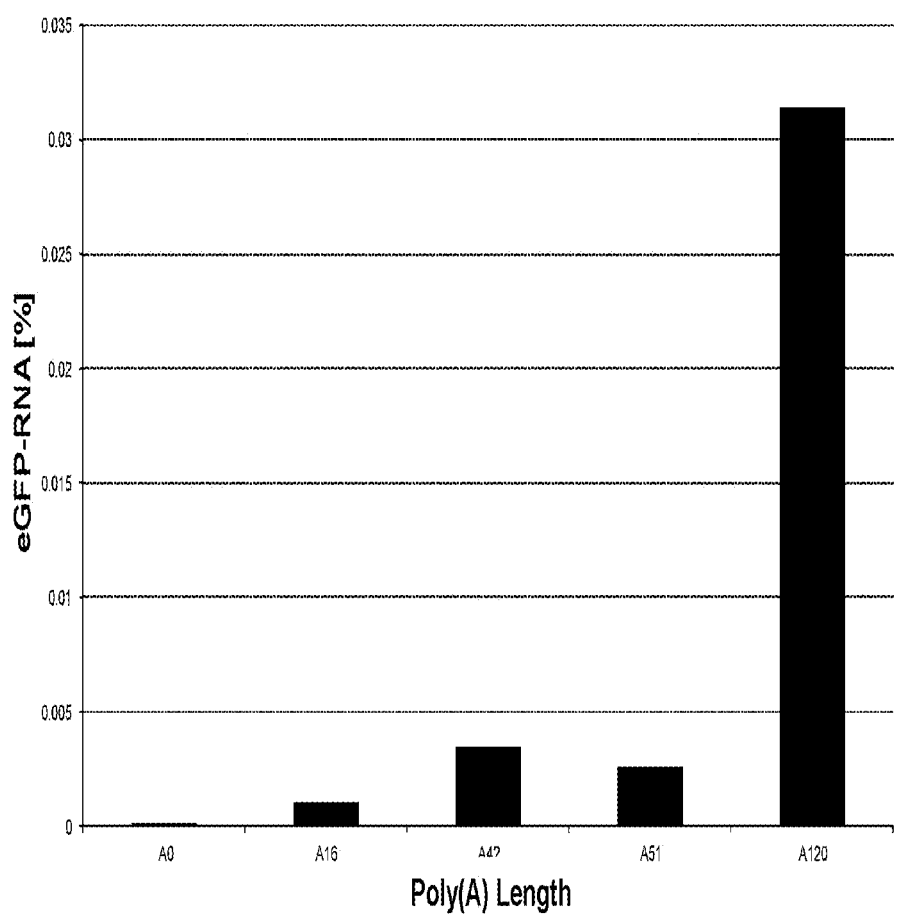

The analysis of RNA having poly(A) sequences of 16 bp, 42 bp, 51 bp, 67 bp, 120 bp, 200 bp, 300 bp and 600 bp in length revealed that extension of said poly(A) sequence up to 120 A nucleotides increases transcript stability and translation and that an extension going beyond that has no positive effect. This effect is observed both in K562 cells and in immature DCs (iDC) (FIGS. 6a and 6b). Extending the poly(A) sequence from 51 to 120 A nucleotides produces a 1.5 to 2-fold increase in translation efficiency. This effect is also reflected in RNA stability (FIG. 6c).

c. Effect of the Occurrence of a 3'-Untranslated Region on RNA Translation and Stability A time course with K562 cells and immature DCs confirmed that introducing a 3'-untranslated region (UTR) of human beta-globin results in increasing expression of an RNA transcript. In addition, it was demonstrated that a double 3'-untranslated region (UTR) of human beta-globin results in an enhanced level of expression after 24 h, which markedly exceeds the combined effect of two individual UTRs (FIG. 7).

d. Effect of a Combination of the Above-Described Modifications on RNA Translation and Stability According to the invention, a combination of the above-described modifications in an RNA transcript was shown to increase the translation efficiency of eGFP in immature and also in mature DCs by a factor of greater than five (FIG. 8).

Example 3: Presentation of a Peptide Expressed Via in Vitro-Transcribed RNA with Increased Stability and Translation Efficiency by MHC Molecules According to the invention, the use of RNA constructs modified according to the invention was shown to increase peptide-MHC presentation on the cell surface. To this end, the nucleic acid sequence coding for eGFP in the IVT vectors described was replaced with a nucleic acid sequence coding for the OVA257-264 epitope (SIINFEKL), and the constructs were compared with one another. The target cells used for transfection were EL4 cells (murine, T cell lymphoma).

In order to quantify SIINFEKL peptides presented by MHC molecules, the cells were stained with an anti-H2-K$^b$-OVA257-264 antibody at various time points after electroporation, and the fluorescence intensity of a secondary antibody was determined with the aid of FACS-Kalibur (FIG. 9).

Furthermore, the SIINFEKL peptide was cloned into the vector which reflected all optimizations (pST1-Sec-SIINFEKL-2BgUTR-A120-Sap1) and into a vector with standard features (pST1-Sec-SIINFEKL-A67-Spe1). IVT RNA derived from both vectors was electroporated into EL4 cells and BMDCs. OVA-peptide/K$^b$ complexes were found on the cell surface in substantially greater numbers and were maintained over a longer period of time after electroporation of the RNA modified according to the invention, Sec-SIINFEKL-2-BgUTR-A120 (FIG. 10).

Example 4: Effect of a Transfection of Cells with in Vitro-Transcribed RNA Coding for a Peptide to be Presented on the Expansion of Antigen-Specific T Cells In order to evaluate the effect on stimulatory capacity, OT-I-TCR was employed which had been used intensively in the C57BL/J6 (B6) background in order to detect MHC class I presentation of the SIINFEKL peptide. OT-I CD8$^+$ T cells which are transgenic with regard to the T cell receptor (TCR) and which recognize the K$^b$-specific peptide SIINFEKL from chicken OVA (OVA$_{257-264}$), was kindly provided by H. Schild (Institute of Immunology, University of Mainz, Germany).

On day 0, animals underwent adoptive transfer with OT-I-CD8$^+$ T cells. To this end, splenocytes were prepared from TCR tg OT-I mice and introduced into the tail vein of C57BL/J6 recipient mice. The cell number was adjusted to $1\times10^5$ TCR tg CD8$^+$ T cells. On the next day, $1\times10^6$ BMDCs of C57BL/J6 mice which had been electroporated with 50 pmol of SIINFEKL-encoding RNA construct variants and had been allowed to mature by means of poly(I:C) for 16 hours were administered ip to mice. On day 4, OT-I-CD8$^+$ T cells were measured in peripheral blood with the aid of the tetramer technology. To this end, retroorbital blood samples were taken and stained with anti-CD8 (Caltag Laboratories, Burlingame, USA) and SIINFEKL tetramer (H-2Kb/SIINFEKL 257-264; Beckman Coulter, Fullerton, USA).

Figure 11A:
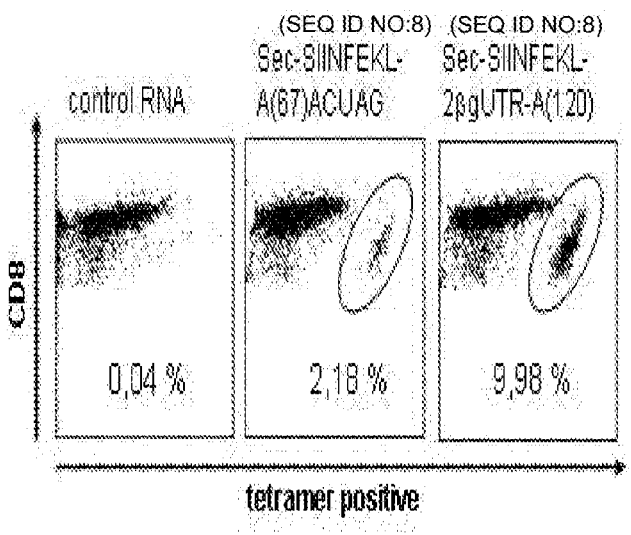

In vivo expansion of antigen-specific TCR-transgenic CD8$^+$ T cells was found to be substantially improved when using Sec-SIINFEKL-2BgUTR-A120 RNA for antigen supply in comparison with Sec-SIINFEKL-A67-ACUAG RNA (FIG. 11A).

Figure 11B:
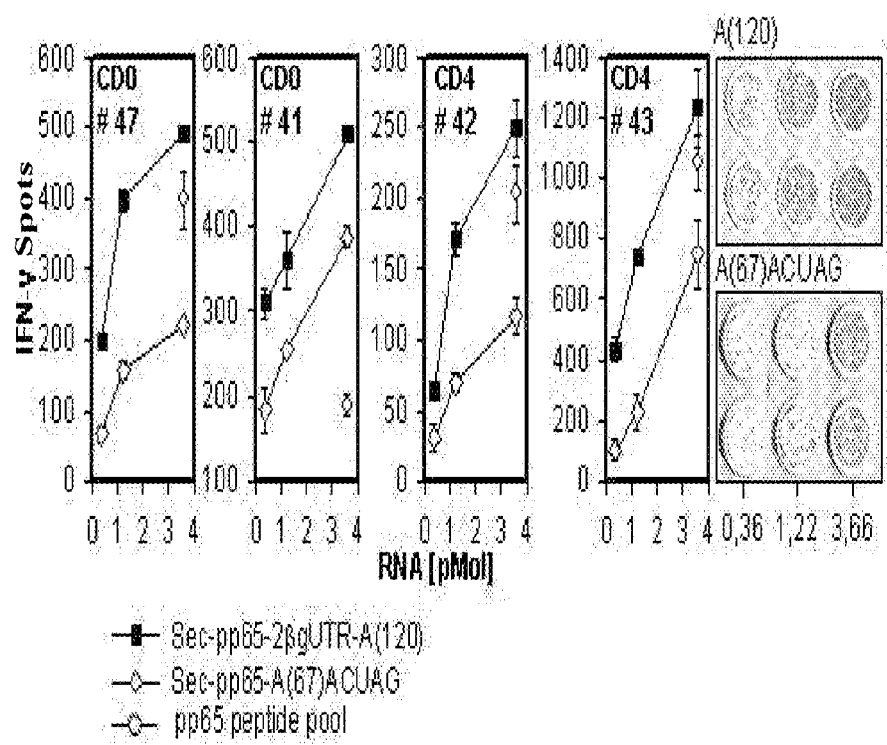

In order to evaluate, whether stabilized IVT RNA constructs for antigen supply also improve antigen-specific stimulation of human T cells, HCMV-pp65, the immunodominant antigen of human cytomegalovirus which is often used for validating autologous stimulation of polyepitopic T cell reactions, was employed. CD4$^+$ and CD8$^+$ T cells which had been purified from HCMV-seropositive healthy donors by positive magnetic cell sorting by means of antibody-coated microbeads (Miltenyi Biotec, Bergisch-Gladbach, Germany) were cocultured with $2\times10^5$ autologous DCs which had been electroporated with the corresponding IVT RNA variants coding for pp65. An expansion of T cells, measured on day 7 in an IFN-γ-ELISpot using autologous DCs which had been pulsed with a pool of overlapping peptides covering the entire pp65 protein sequence, or with a control protein, demonstrated the superiority of Sec-pp65-2BgUTR-A120, with the effects with regard to expansion of CD4+ T cells being the most pronounced (FIG. 11B).

REFERENCES

Bargmann, C. I., Hung, M. C., and Weinberg, R. A. (1986). The neu oncogene encodes an epidermal growth factor receptor-related protein. Nature 319, 226-230.

Boczkowski, D., Nair, S. K., Nam, J. H., Lyerly H. K., and Gilboa, E. (2000). Induction of tumor immunity and cytotoxic T lymphocyte responses using dendritic cells transfected with messenger RNA amplified from tumor cells. Cancer Res. 60, 1028-1034.

Carralot, J. P., Probst, J., Hoerr, I., Scheel, B., Teufel, R., Jung, G., Rammensee, H. G., and Pascolo, S. (2004). Polarization of immunity induced by direct injection of naked sequence-stabilized mRNA vaccines. Cell Mol. Life Sci. 61, 2418-2424.

Condon, C., Watkins, S. C., Celluzzi, C. M., Thompson, K., and Falo, L. D., Jr. (1996). DNA-based immunization by in vivo transfections of dendritic cells. Nat. Med. 2, 1122-1128.

Conry, R. M., LoBuglio, A. F., Kantor, J., Schlom, J., Loechel, F., Moore, S. E., Sumerel, L. A., Barlow, D. L., Abrams, S., and Curiel, D. T. (1994). Immune response to a carcinoembryonic antigen polynucleotide vaccine. Cancer Res. 54, 1164-1168.

Conry, R. M., LoBuglio, A. F., Loechel, F., Moore, S. E., Sumerel, L. A., Barlow, D. L., and Curiel, D. T. (1995a). A carcinoembryonic antigen polynucleotide vaccine has in vivo antitumor activity. Gene Ther. 2, 59-65.

Conry, R. M., LoBuglio, A. F., Wright, M., Sumerel, L., Pike, M. J., Johanning, F., Benjamin, R., Lu, D., and Curiel, D. T. (1995b). Characterization of a messenger RNA polynucleotide vaccine vector. Cancer Res. 55, 1397-1400.

Cox, G. J., Zamb, T. J., and Babiuk, L. A. (1993). Bovine herpesvirus 1: immune responses in mice and cattle injected with plasmid DNA. J. Virol. 67, 5664-5667.

Davis, H. L., Michel, M. L., and Whalen, R. G. (1993). DNA-based immunization induces continuous secretion of hepatitis B surface antigen and high levels of circulating antibody. Hum. Mol. Genet. 2, 1847-1851.

Gallie, D. R. (1991). The cap and poly(A) tail function synergistically to regulate mRNA translational efficiency. Genes Dev. 5, 2108-2116.

Gilkeson, G. S., Pippen, A. M., and Pisetsky, D. S. (1995). Induction of cross-reactive anti-dsDNA antibodies in preautoimmune NZB/NZW mice by immunization with bacterial DNA. J. Clin. Invest. 95, 1398-1402.

Greenblatt, M. S., Bennett, W. P., Hollstein, M., and Harris, C. C. (1994). Mutations in the p53 tumor suppressor gene: clues to cancer etiology and molecular pathogenesis. Cancer Res. 54, 4855-4878.

Heiser, A., Coleman, D., Dannull, J., Yancey, D., Maurice, M. A., Lallas, C. D., Dahm, P., Niedzwiecki, D., Gilboa, E., and Vieweg, J. (2002). Autologous dendritic cells transfected with prostate-specific antigen RNA stimulate CTL responses against metastatic prostate tumors. J. Clin. Invest 109, 409-417.

Heiser, A., Dahm, P., Yancey, D. R., Maurice, M. A., Boczkowski, D., Nair, S. K., Gilboa, E., and Vieweg, J. (2000). Human dendritic cells transfected with RNA encoding prostate-specific antigen stimulate prostate-specific CTL responses in vitro. J. Immunol. 164, 5508-5514.

Hoerr, I., Obst, R., Rammensee, H. G., and Jung, G. (2000). In vivo application of RNA leads to induction of specific cytotoxic T lymphocytes and antibodies. Eur. J. Immunol. 30, 1-7.

Malone, R. W., Felgner, P. L., and Verma, I. M. (1989). Cationic liposome-mediated RNA transfection. Proc. Natl. Acad. Sci. USA 86, 6077-6081.

Preiss, T. and Hentze, M. W. (1998). Dual function of the messenger RNA cap structure in poly(A)-tail promoted translation in yeast. Nature 392, 516-520.

Spooner, R. A., Deonarain, M. P., and Epenetos, A. A. (1995). DNA vaccination for cancer treatment. Gene Ther. 2, 173-180.

Strong, T. V., Hampton, T. A., Louro, I., Bilbao, G., Conry, R. M., and Curiel, D. T. (1997). Incorporation of beta-globin untranslated regions into a Sindbis virus vector for augmentation of heterologous mRNA expression. Gene Ther. 4, 624-627.

Su, Z., Dannull, J., Heiser, A., Yancey, D., Pruitt, S., Madden, J., Coleman, D., Niedzwiecki, D., Gilboa, E., and Vieweg, J. (2003). Immunological and clinical responses in metastatic renal cancer patients vaccinated with tumor RNA-transfected dendritic cells. Cancer Res. 63, 2127-2133.

Tang, D. C., DeVit, M., and Johnston, S. A. (1992). Genetic immunization is a simple method for eliciting an immune response. Nature 356, 152-154.

Teufel, R., Carralot, J. P., Scheel, B., Probst, J., Walter, S., Jung, G., Hoerr, I., Rammensee, H. G., and Pascolo, S. (2005). Human peripheral blood monuclear cells transfected with messenger RNA stimulate antigen-specific cytotoxic T-lymphocytes in vitro. Cell Mol. Life Sci. 62, 1755-1762.

Ulmer, J. B., Donnelly, J. J., Parker, S. E., Rhodes, G. H., Felgner, P. L., Dwarki, V. J., Gromskowski, S. H., Deck, R. R., DeWitt, C. M., Friedman, A., et al. (1993). Heterologous protection against influenza by injection of DNA encoding a viral protein. Science 259, 1745-1749.

Wang, B., Merva, M., Dang, K., Ugen, K. E., Williams, W. V., and Weiner, D. B. (1995). Immunization by direct DNA inoculation induces rejection of tumor cell challenge. Hum. Gene Ther. 6, 407-418.

Wang, B., Ugen, K. E., Srikantan, V., Agadjanyan, M. G., Dang, K., Refaeli, Y., Sato, A. I., Boyer, J., Williams, W. V., and Weiner, D. B. (1993). Gene inoculation generates immune responses against human immunodeficiency virus type 1. Proc. Natl. Acad. Sci. USA 90, 4156-4160.

Wolff, J. A., Malone, R. W., Williams, P., Chong, W., Acsadi, G., Jani, A., and Felgner, P. L. (1990). Direct gene transfer into mouse muscle in vivo. Science 247, 1465-1468.

Ying, H., Zaks, T. Z., Wang, R. F., Irvine, K. R., Kammula, U.S., Marincola, F. M., Leitner, W. W., and Restifo, N. P. (1999). Cancer therapy using a self-replicating RNA vaccine. Nat. Med. 5, 823-827.

SEQUENCE LISTING

```
Sequence total quantity: 8
SEQ ID NO: 1                  moltype = DNA   length = 142
FEATURE                       Location/Qualifiers
source                        1..142
                              mol_type = other DNA
                              organism = Homo sapiens
SEQUENCE: 1
agctcgcttt cttgctgtcc aatttctatt aaaggttcct tgttccccta agtccaacta   60
ctaaactggg ggatattatg aagggccttg agcatctgga ttctgcctaa taaaaaacat  120
ttattttcat tgctgcgtcg ag                                           142

SEQ ID NO: 2                  moltype = DNA   length = 17
FEATURE                       Location/Qualifiers
misc_feature                  1..17
                              note = Type II vector 5 prime Poly(A)-SpeI
source                        1..17
                              mol_type = other DNA
                              organism = synthetic construct
SEQUENCE: 2
aaaaaaaaaa ctagtct                                                  17

SEQ ID NO: 3                  moltype = DNA   length = 17
FEATURE                       Location/Qualifiers
misc_feature                  1..17
                              note = Type II Vector 3 prime Poly(A)-SpeI
source                        1..17
                              mol_type = other DNA
                              organism = synthetic construct
SEQUENCE: 3
agactagttt ttttttt                                                  17

SEQ ID NO: 4                  moltype = DNA   length = 14
FEATURE                       Location/Qualifiers
misc_feature                  1..14
                              note = Type II Poly(A)-SpeI template
source                        1..14
                              mol_type = other DNA
                              organism = synthetic construct
SEQUENCE: 4
tttttttttt gatc                                                     14

SEQ ID NO: 5                  moltype = RNA   length = 14
FEATURE                       Location/Qualifiers
misc_feature                  1..14
                              note = Type II RNA Poly(A)-SpeI
source                        1..14
                              mol_type = other RNA
                              organism = synthetic construct
SEQUENCE: 5
aaaaaaaaaa ctag                                                     14

SEQ ID NO: 6                  moltype = DNA   length = 19
FEATURE                       Location/Qualifiers
misc_feature                  1..19
                              note = Type IIS Vector 5 prime Poly(A)-SapI
source                        1..19
                              mol_type = other DNA
                              organism = synthetic construct
SEQUENCE: 6
aaaaaaaaaa aagaagagc                                                19

SEQ ID NO: 7                  moltype = DNA   length = 19
FEATURE                       Location/Qualifiers
misc_feature                  1..19
                              note = Type IIS Vector 3 prime Poly(A)-SapI
source                        1..19
                              mol_type = other DNA
                              organism = synthetic construct
SEQUENCE: 7
gctcttcttt ttttttt                                                  19
```

```
SEQ ID NO: 8           moltype = AA  length = 8
FEATURE                Location/Qualifiers
source                 1..8
                       mol_type = protein
                       organism = synthetic construct
SEQUENCE: 8
SIINFEKL                                                                        8
```

The invention claimed is:
1. An immunogenic composition comprising:
an mRNA molecule comprising, in a 5' to 3' orientation:
   (a) a 5' cap,
   (b) a sequence that encodes an antigen and ends with a termination codon,
   (c) a 3'-untranslated region (3'-UTR) extending from the termination codon to a 3'-terminal poly(A) tail sequence consisting of 100 to 150 consecutive A nucleotides,
   wherein the 3'-terminal nucleotide of the mRNA molecule is an A nucleotide of the poly(A) tail sequence;
   wherein the 3'-UTR is heterologous with respect to the sequence that encodes the antigen.

2. The immunogenic composition of claim 1, wherein upon delivery of the immunogenic composition into a mammalian cell, the stability and/or translation efficiency of the mRNA molecule is increased, as compared to that of an mRNA molecule without the 3'-terminal poly(A) tail sequence (c).

3. The immunogenic composition of claim 1, wherein the 3'-terminal poly(A) tail sequence has a length of 100 consecutive A nucleotides.

4. The immunogenic composition of claim 1, wherein the 3'-terminal poly(A) tail sequence has a length of 120 consecutive A nucleotides.

5. The immunogenic composition of claim 1, wherein the 3'-UTR comprises a 3' UTR of a globin gene.

6. The immunogenic composition of claim 1, wherein the mRNA molecule comprises a non-natural nucleotide analog.

7. The immunogenic composition of claim 1, wherein the antigen comprises a tumor antigen.

8. The immunogenic composition of claim 1, wherein the mRNA molecule is an in vitro transcribed mRNA molecule.

9. The immunogenic composition of claim 1, wherein the antigen comprises a peptide or protein.

10. An isolated mammalian cell comprising:
an mRNA molecule comprising, in a 5' to 3' orientation:
   (a) a 5' cap,
   (b) a sequence that encodes a peptide or a protein and ends with a termination codon,
   (c) a 3'-untranslated region (3'-UTR) extending from the termination codon to a 3'-terminal poly(A) tail sequence consisting of 100 to 150 consecutive A nucleotides,
   wherein the 3'-terminal nucleotide of the mRNA molecule is an A nucleotide of the poly(A) tail sequence;
   wherein the 3'-UTR is heterologous with respect to the sequence that encodes the peptide or the protein; and
   wherein stability and/or translation efficiency of the mRNA molecule is increased as compared to that of an mRNA molecule with a poly(A) tail sequence that is shorter than 100 consecutive A nucleotides.

11. The isolated mammalian cell of claim 10, wherein the 3'-terminal poly(A) tail sequence has a length of 100 consecutive A nucleotides.

12. The isolated mammalian cell of claim 10, wherein the mRNA molecule comprises at least one of the following features:
a non-natural nucleotide analog; or
a 3'-UTR that comprises a 3'-UTR of a globin gene; and
a 3'UTR that comprises a ribosome binding sequence.

13. The isolated mammalian cell of claim 10, wherein the mRNA molecule is an in vitro transcribed mRNA molecule.

14. The isolated mammalian cell of claim 10, wherein the peptide or protein comprises an antigen.

15. The isolated mammalian cell of claim 10, wherein the 3'-terminal poly(A) tail sequence has a length of 120 consecutive A nucleotides.

16. An isolated antigen-presenting cell comprising:
an mRNA molecule comprising, in a 5' to 3' orientation:
   (b) a sequence that encodes a peptide or a protein and ends with a termination codon,
   (c) a 3'-untranslated region (3'-UTR) extending from the termination codon to a 3'-terminal poly(A) tail sequence consisting of 100 to 150 consecutive A nucleotides,
   wherein the 3'-terminal nucleotide of the mRNA molecule is an A nucleotide of the poly(A) tail sequence;
   wherein the 3'-UTR is heterologous with respect to the sequence encoding the peptide or the protein.

17. The isolated antigen-presenting cell of claim 16, wherein the antigen-presenting cell is a dendritic cell.

18. The isolated antigen-presenting cell of claim 16, wherein the peptide or the protein comprises an antigen.

19. The isolated antigen-presenting cell of claim 16, wherein the 3'-terminal poly(A) tail sequence has a length of 100 consecutive A nucleotides.

20. The isolated antigen-presenting cell of claim 16, wherein the mRNA molecule comprises at least one of the following features:
a non-natural nucleotide analog; or
a 3'-UTR that comprises a 3'-UTR of a globin gene.

21. The isolated antigen-presenting cell of claim 16, wherein the mRNA molecule is an in vitro transcribed mRNA molecule.

22. The isolated antigen-presenting cell of claim 16, wherein stability and/or translation efficiency of the mRNA molecule is increased as compared to that of an mRNA molecule with a poly(A) tail sequence consisting of no more than 51 consecutive A nucleotides.

23. The isolated antigen-presenting cell of claim 16, wherein the 3'-terminal poly(A) tail sequence has a length of 120 consecutive A nucleotides.

24. A method for stimulating or expanding antigen-specific T cells, the method comprising steps of:
   (a) obtaining an mRNA molecule comprising, in a 5' to 3' orientation:
      (i) a 5' cap,
      (ii) a sequence that encodes an antigen and ends with a termination codon, (iii) a 3'-untranslated region (3'-UTR) extending from the termination codon to a 3'-terminal poly(A) tail sequence consisting of 100 to 150 consecutive A nucleotides,
  wherein the 3'-terminal nucleotide of the mRNA molecule is an A nucleotide of the poly(A) tail sequence;
  wherein the 3'-UTR is heterologous with respect to the sequence that encodes the antigen;
(b) delivering the mRNA molecule to antigen-presenting cells under conditions such that the encoded antigen is expressed in the antigen-presenting cells; and
(c) exposing T cells to the antigen-presenting cells from (b) under conditions that stimulate or expand antigen-specific T cells, wherein the number of antigen-specific T cells is increased, as compared to that of an mRNA molecule having a poly(A) tail sequence of no more than 51 consecutive A nucleotides.

25. The method of claim 24, wherein the T cells comprise CD4+ and/or CD8+ T cells, and/or wherein the antigen-presenting cells are or comprise dendritic cells.

26. The method of claim 24, wherein the mRNA molecule is delivered to the antigen-presenting cells by transfection in vitro.

27. The method of claim 24, wherein stability and/or translation efficiency of the mRNA molecule is increased as compared to that of an mRNA molecule with a poly(A) tail sequence of 51 consecutive A nucleotides.

28. A method of producing in vitro an mRNA molecule suitable for use as a pharmaceutical, the method comprising steps of:
  (i) obtaining a nucleic acid molecule comprising (a) a first nucleic acid sequence which codes for a nucleotide sequence comprising 100 to 150 consecutive A nucleotides, (b) a second nucleic acid sequence which is transcribable into mRNA, wherein the first nucleic acid sequence is located at the 3' end of the second nucleic acid sequence, and (c) a recognition sequence for a type IIS restriction endonuclease that is located 3' of the first nucleic acid sequence such that the corresponding cleavage site for the type IIS restriction endonuclease is located within the first nucleic acid sequence;
  (ii) cleaving the first nucleic acid sequence of the nucleic acid molecule from step (i) with a type IIS restriction endonuclease; and
  (iii) transcribing in vitro the nucleic acid molecule obtained after step (ii) thereby forming a transcript which comprises the mRNA transcribed from the second nucleic acid sequence and a 3-terminal nucleotide sequence of 100 to 150 consecutive A nucleotides, wherein the 3-terminal nucleotide of said transcript is an A nucleotide, and
wherein the transcript formed from step (iii) is characterized in that upon delivery into a mammalian cell, the stability and/or translation efficiency of the transcript is increased, as compared to that of a transcript without the 3'-terminal nucleotide sequence of 100 to 150 consecutive A nucleotides.

29. A method of increasing the stability of an in vitro-transcribed mRNA molecule, the method comprising steps of:
  (i) obtaining a nucleic acid molecule comprising (a) a first nucleic acid sequence which, when transcribed, codes for a nucleotide sequence comprising 100 to 150 consecutive A nucleotides, (b) a second nucleic acid sequence which is transcribable into mRNA, wherein the first nucleic acid sequence is located at the 3' end of the second nucleic acid sequence, and (c) a recognition sequence for a type IIS restriction endonuclease, that is located 3' of the first nucleic acid sequence, such that the corresponding cleavage site for the type IIS restriction endonuclease is located within the first nucleic acid sequence;
  (ii) cleaving the first nucleic acid sequence of the nucleic acid molecule from step (i) with a type IIS restriction endonuclease; and
  (iii) transcribing in vitro the nucleic acid molecule obtained after step (ii) thereby forming a transcript which comprises the mRNA transcribed from the second nucleic acid sequence and a 3-terminal nucleotide sequence of 100 to 150 consecutive A nucleotides, wherein the 3-terminal nucleotide of said transcript is an A nucleotide, wherein stability of the transcript is greater than that of a transcript without a 3'-terminal nucleotide sequence of 100 to 150 consecutive A nucleotides.

30. A method of increasing the expression efficiency of an mRNA transcript, the method comprising steps of:
  (i) obtaining an mRNA transcript comprising a coding sequence that encodes a peptide or a protein and a 3-terminal nucleotide sequence of 100 to 150 consecutive A nucleotides, wherein the 3-terminal nucleotide of the mRNA transcript is an A nucleotide; and
  (ii) delivering the mRNA transcript to cells under conditions such that the peptide or protein encoded by the coding sequence is expressed in the cells, wherein expression efficiency of the coding sequence and thereby amount of the peptide or protein encoded by the coding sequence is increased as compared to that of the coding sequence of an mRNA transcript without a 3'-terminal nucleotide sequence of 100 to 150 consecutive A nucleotides.

\* \* \* \* \*